United States Patent
Fukuchi et al.

(10) Patent No.: US 9,024,262 B2
(45) Date of Patent: May 5, 2015

(54) PET DEVICE AND IMAGING METHOD THEREFOR

(75) Inventors: Tomonori Fukuchi, Kobe (JP); Shuichi Enomoto, Okayama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 14/236,847

(22) PCT Filed: Aug. 1, 2012

(86) PCT No.: PCT/JP2012/069572
§ 371 (c)(1),
(2), (4) Date: Feb. 3, 2014

(87) PCT Pub. No.: WO2013/018825
PCT Pub. Date: Feb. 7, 2013

(65) Prior Publication Data
US 2014/0175293 A1 Jun. 26, 2014

(30) Foreign Application Priority Data
Aug. 3, 2011 (JP) .................. 2011-169839

(51) Int. Cl.
*G01T 1/20* (2006.01)
*G01T 1/29* (2006.01)
*A61B 6/03* (2006.01)

(52) U.S. Cl.
CPC ............. *G01T 1/2985* (2013.01); *A61B 6/037* (2013.01)

(58) Field of Classification Search
USPC .......................... 250/362, 363.04
See application file for complete search history.

(56) References Cited

U.S. PATENT DOCUMENTS

| 4,833,327 A | 5/1989 | Hart |
| 8,076,645 B2 | 12/2011 | Motomura et al. |

(Continued)

FOREIGN PATENT DOCUMENTS

| JP | 2008045948 A | 2/2008 |
| JP | 2010156673 A | 7/2010 |
| WO | 2007105536 A1 | 9/2007 |

OTHER PUBLICATIONS

Author:Krzysztof Kacperski et al., Title: Three-Gamma Annihilation Imaging in Positron Emission Tomography, Date: Apr. 2004, Publisher: IEEE Transactions on Medical Imaging, vol. 23, No. 4.*

(Continued)

*Primary Examiner* — David J Makiya
*Assistant Examiner* — Taeho Jo
(74) *Attorney, Agent, or Firm* — Seed IP Law Group PLLC

(57) ABSTRACT

In the present invention, to conduct multiple molecular imaging in a PET device, both a first probe and a second probe, each of which has a nuclide that emits unique gamma rays as a result of gamma decay after beta decay, are administered to a subject to be imaged, and then the image capturing is performed by a multiple probe PET device (100). The multiple probe PET device (100) is provided with a group of PET gamma ray detectors (10) and an energy-resolving gamma ray detector (20), and, when an imaging processor (30) executes image reconstruction based on a pair-annihilation detection signal from the group of PET gamma ray detectors (10), images are reconstructed differently according to the energy values of the unique gamma rays. Imaging can also be carried out using a nuclide that does not emit any unique gamma ray and a nuclide that emits a unique gamma ray.

28 Claims, 13 Drawing Sheets

(56) References Cited

U.S. PATENT DOCUMENTS

| | | | |
|---|---|---|---|
| 2004/0227091 A1* | 11/2004 | LeBlanc et al. | 250/366 |
| 2007/0040115 A1* | 2/2007 | Publicover et al. | 250/305 |
| 2009/0012718 A1 | 1/2009 | Ohtani et al. | |
| 2009/0108206 A1* | 4/2009 | Breuer et al. | 250/363.03 |
| 2009/0169082 A1* | 7/2009 | Mizuta et al. | 382/131 |
| 2009/0218502 A1* | 9/2009 | Axelsson et al. | 250/370.11 |
| 2013/0062526 A1* | 3/2013 | Tsuda et al. | 250/362 |
| 2014/0061483 A1* | 3/2014 | Yoshida et al. | 250/362 |

OTHER PUBLICATIONS

Kurfess et al., "Coincident Compton Nuclear Medical Imager," IEEE Nuclear Science Symposium Conference Record, vol. 2, 2001, pp. 1166-1170.

International Search Report, for PCT/JP2012/069572, mailed Nov. 6, 2012, 4 pages.

Zeng, "Medical Image Reconstruction: A Conceptual Tutorial," Springer-Verlag, 87-173 (101 pages), 2010.

* cited by examiner (a) Type-A (b) Type-B (a)

(b)

PET DEVICE AND IMAGING METHOD THEREFOR

TECHNICAL FIELD

The present invention relates to a PET device and an imaging method thereof. More specifically, the present invention relates to a PET device and an imaging method thereof for simultaneously imaging a plurality of probes that accumulates in portions of a subject to be imaged.

BACKGROUND ART

Recent developments of medical technologies include noninvasive imaging techniques of tracer molecule's distribution in vivo using tomography. For example, positron emission tomography (PET) devices are utilized as one of diagnostic apparatuses in the field of nuclear medicine. In PET devices, detection is made for two pencils of gamma rays, or hereinafter "pair-annihilation gamma rays," which are emitted when a positron emitted through beta decay ($\beta^+$ decay, or positron decay) makes pair-annihilation with an electron in surrounding media. The pair-annihilation gamma rays are a pair of gamma rays that are emitted into opposite directions of substantially 180 degrees therebetween, each of which has energy of 511 keV. In the PET devices, a number of straight lines are identified, each of which connecting a pair of detectors that detected the pair-annihilation gamma rays, and thereby a distribution is estimated for a nuclide that make transitions with the beta decay. For example, molecules of a medical agent that accumulate in cancer cells are labeled with a positron emitting nuclide and imaging the living body, or the subject to be imaged, to which the medical agent has been administered, by the PET device; then a three dimensional in vivo distribution image of the cancer cells is obtained. Compared to a single photon emission computed tomography (SPECT), which is also a diagnostic imaging device in nuclear medicine like the PET device for imaging in vivo functional images of the living body, the PET device is generally superior in sensitivity and qualitative performance, because PET devices do not require any collimator for gamma rays.

On the other hand, according to the developments in life science or biomedical science it has been revealed that complex interrelated dynamics among a plurality of molecules is actually underlying the activities of living organisms, and would be related to initiation of lesions. What has been studied in anticipation of such applications is administering multiple medicines labeled with different radioactive nuclides to obtain distribution images of respective medicines at a time ("simultaneous imaging on multi-tracer"). To realize the simultaneous imaging on multi-tracer, such techniques as SPECT and use of Compton cameras are adopted.

On the other hand, a technique is disclosed for detecting gamma rays emitted in a gamma decay that takes place following a positron decay, where energy of each gamma ray is specific to nuclide, or "a unique gamma ray," and where the detection is made together with the pair-annihilation gamma rays of the positron decay. For example, Non-Patent Document 1 (James D. Kurfess et al, IEEE Nuclear Science Symposium Conference Record, 2001 vol. 2 p. 1166-1170) and Patent Document 1 (U.S. Pat. No. 4,833,327) disclose improving resolution of PET images by using unique gamma rays from a single nuclide.

REFERENCES

Patent Document

Patent Document 1: U.S. Pat. No. 4,833,327

Non-Patent Documents

Non-Patent Document 1: James D. Kurfess and Bernard F. Phlips, "Coincident Compton Nuclear Medical Imager", IEEE Nuclear Science Symposium Conference Record, 2001 vol. 2 p. 1166-1170

Non-Patent Document 2: Genqsheng Lawrence Zeng, "Medical Image Reconstruction: A Conceptual Tutorial", Springer-Verlag, 2010

SUMMARY OF THE INVENTION

Technical Problem

Nuclides that are used for labeling probes in conventional PET devices are positron emitting nuclides, such as $^{11}$C, $^{15}$O, and $^{18}$F, and radiations detected for such nuclides are gamma rays that are emitted into opposite directions forming substantially 180 degrees each other upon pair annihilations of positrons emitted through beta decays. The pair-annihilation nuclides have energy of 511 keV regardless of the nuclides, which corresponds to rest masses of a positron and an electron. Therefore, in general PET devices using conventional pair-annihilation gamma rays, even if a plurality types of probes are administered to living body at a time, no distinction among different probes can be made in principle when imaging their distributions. It should also be noted that, to carry out simultaneous imaging of multi probes, a technique that uses difference in the radioactive decay among different probes is known. This technique identifies probes having different decay time based on the time dependence of the captured images. However, this technique does not directly identify multiple probes; among other things, it is difficult to perform imaging for targets in which distributions are dependent on time, or to perform imaging of their dynamics.

The number of probes in techniques for detecting the unique gamma rays mentioned above, such as in Non-Patent Document 1 or Patent Document 1, is one at the maximum. Non-Patent Document 1 and Patent Document 1 fail to disclose simultaneous imaging differently on multi-tracer for simultaneous imaging a plurality of probes that distribute to respective regions in vivo differently, or to disclose specific technology for such purposes.

Moreover, when imaging by SPECT, a planer detector with a collimator detects a single gamma ray created by gamma decay and coming from a specified direction; thereby a projection image of distribution of the gamma ray source is obtained. To obtain two or three dimensional distribution of gamma ray sources in SPECT, image reconstruction has to be done by plural devices or by rotating a device to have projection images in multiple directions. Therefore, it would be possible in the SPECT to image multiple nuclides simultaneously where the nuclides have different energy values for respective unique gamma rays. However, since it is imperative to use collimators for gamma rays in the SPECT by its nature, accuracy of the image will be degraded for unique gamma rays of higher energy, such as 300 keV or more. Consequently, nuclides applicable to the SPECT are limited to those that emit gamma rays of lower energy. For simultaneous imaging on multi-tracer in the SPECT, this means not only that applicable nuclides are limited, but that multiple gamma ray sources should be selected from ones in a narrow energy range. It follows that, the energy values of gamma rays become so close with each other that it would be highly probable that differentiation among gamma rays is difficult. On top of that, the SPECT is inferior in performances of sensitivity, quantitativeness, and resolution to PET devices as mentioned above.

The Compton cameras are also studied intensively in many institutions, because they are considered advantageous in the simultaneous imaging on multi-tracer. However, in comparison with the conventional PET devices, such Compton cameras are inferior in performances of sensitivity, quantitativeness, and resolution.

The present invention has been made to solve at least any of such problems as stated above. The present invention contributes to developments in advanced biological research activities and clinical diagnose applications by providing PET devices that can conduct probe distribution imaging with differentiation among probes for a subject to which multiple probes are administered, to an extent that would never have been possible with imaging only with a single medical agent. In addition to the life science, the present invention contributes to other technological fields by providing a general method of simultaneous imaging on multi-tracer as, to name a few, non-destructive testing or nuclear materials detection for security.

Solution to Problem

The inventors of the present application have found that it is possible to perform simultaneous multi-tracer imaging while taking advantages of high resolution capability of PET devices, by adopting nuclides having different decay schemes each other for labeling the probes that will be administered to a subject to be imaged with the PET device. The nuclides adopted in the present invention are ones that emit unique gamma rays while they are positron emitting nuclides. That is, they are, among other positron emitting nuclides, those that emit a positron through beta decay, and thereafter emit unique gamma rays trough gamma decay. In one embodiment of the present invention, a plurality of such nuclides is adopted, whereas in another embodiment of the present invention, a nuclide of such a type and a conventional nuclide that emits a positron only through beta decay are adopted. In either embodiment, unique gamma ray detection following pair-annihilation gamma rays detection enables identification as to which nuclide has actually emitted the pair-annihilation gamma rays. Therefore, even when multiple probes labeled by respective nuclides are administered to a subject to be imaged at a time, it is possible to capture the image while differentiating them.

Accordingly, in one aspect of the present invention, provided is a positron emission tomography (PET) device for imaging a plurality of probes comprising: a group of PET gamma ray detectors adapted to receive a pair of pair-annihilation gamma rays from a subject to be imaged, wherein the pair of pair-annihilation gamma rays are generated by a positron-electron pair annihilation, and wherein to the subject to be imaged both of a first probe and a second probe are administered, the first probe having a positron emitting nuclide that becomes an excited state of a daughter nuclide through beta decay and, following a positron emission by the beta decay emits a unique gamma ray of a first energy during transition into a ground state of the daughter nuclide, and the second probe having a nuclide that becomes an excited state of a daughter nuclide through beta decay and, following a positron emission by the beta decay, emits a unique gamma ray of a second energy during transition into a ground state of the daughter nuclide, an energy-resolving gamma ray detector adapted to detect one of the unique gamma rays for resolving the first energy and the second energy; and an imaging processor that receives both of a pair-annihilation detection signal supplied according to coincidence measurement with a pair of PET gamma ray detectors in the group of PET gamma ray detectors and a signal supplied by the energy-resolving gamma ray detector, wherein the imaging processor executes reconstruction of images for the pair-annihilation detection signal differently according to whether an energy value of a unique gamma ray detected within a predetermined time of the detection of the pair-annihilation gamma rays corresponds to the first energy or the second energy.

In another aspect of the present invention, provided is a positron emission tomography (PET) device for imaging a plurality of probes comprising: a group of PET gamma ray detectors adapted to receive a pair of pair-annihilation gamma rays from a subject to be imaged, wherein the pair of pair-annihilation gamma rays are generated by a positron-electron pair annihilation, and wherein to the subject to be imaged both of a first probe and a PET probe are administered, the first probe having a nuclide that becomes an excited state of a daughter nuclide through beta decay and, following a positron emission by the beta decay emits a unique gamma ray during transition into a ground state of the daughter nuclide, and the PET probe having a positron emitting nuclide that mainly becomes a ground state of a daughter nuclide through beta decay, an energy-resolving gamma ray detector adapted to receive the unique gamma ray emitted by the first probe; and an imaging processor that receives both of a pair-annihilation detection signal supplied according to coincidence measurement with a pair of PET gamma ray detectors in the group of PET gamma ray detectors and a signal supplied by the energy-resolving gamma ray detector, wherein the imaging processor executes reconstruction of images for the pair-annihilation detection signal differently according to whether detection of the pair-annihilation gamma rays and detection of the unique gamma ray occurred within a predetermined time or not.

The present invention may be practiced in yet another aspect. That is, in the yet another aspect of the present invention, provided is a method for imaging a plurality of probes in a positron emission tomography (PET) device comprising steps of: coincidence measurement using a group of PET gamma ray detectors for a pair of pair-annihilation gamma rays from a subject to be imaged, wherein the pair of pair-annihilation gamma rays have been generated by a positron-electron pair annihilation, and wherein to the subject to be imaged both of a first probe and a second probe were administered, the first probe having a nuclide that becomes an excited state of a daughter nuclide through beta decay and, following a positron emission by the beta decay, emits a unique gamma ray of a first energy during transition into a ground state of the daughter nuclide, and the second probe having a nuclide that becomes an excited state of a daughter nuclide through beta decay and, following a positron emission by the beta decay, emits a unique gamma ray of a second energy during transition into a ground state of the daughter nuclide, performing measurement using an energy-resolving gamma ray detector that is adapted to detect one of the unique gamma rays for resolving the first energy and the second energy, and imaging processing for receiving both of a pair-annihilation detection signal supplied according to the coincidence measurement with a pair of PET gamma ray detectors in the group of PET gamma ray detectors and a signal supplied by the energy-resolving gamma ray detector, and for executing reconstruction of images for the pair-annihilation detection signal differently according to whether an energy value of a unique gamma ray detected within a predetermined time of the detection of the pair-annihilation gamma rays corresponds to the first energy or the second energy.

In yet another aspect of the present invention, provided is a method for imaging a plurality of probes in a positron emission tomography (PET) device comprising steps of: coincidence measurement using a group of PET gamma ray detectors for a pair of pair-annihilation gamma rays from a subject to be imaged, wherein the pair of pair-annihilation gamma rays have been generated by a positron-electron pair annihilation, and wherein to the subject to be imaged both of a first probe and a PET probe were administered, the first probe having a nuclide that becomes an excited state of a daughter nuclide through beta decay and, following a positron emission by the beta decay, emits a unique gamma ray during transition into a ground state of the daughter nuclide, and the PET probe having a positron emitting nuclide that mainly becomes a ground state of a daughter nuclide through the beta decay; performing measurement using an energy-resolving gamma ray detector for the unique gamma ray emitted by the first probe; and imaging processing for receiving both of a pair-annihilation detection signal supplied according to the coincidence measurement with a pair of PET gamma ray detectors in the group of PET gamma ray detectors and a signal supplied by the energy-resolving gamma ray detector, and for executing reconstruction of images for the pair-annihilation detection signal differently according to whether detection of the pair-annihilation gamma rays and detection of the unique gamma ray occurred within a predetermined time or not.

In the aspects of the present invention, beta decay refers $\beta^+$ decay (positron decay) that is accompanied by a positron emission. A daughter nuclide means a nuclide after nuclidic decay, through which an atomic number is varied from one for a radioactive nuclide (parent nuclide). Both nuclides used for labeling the first and second probes make nuclidic transitions via beta decay accompanied by positron emission to an excited state of respective daughter nuclide, and, following that, emit their excitation energy values that are unique to respective nuclides in a form of gamma rays when making transition respectively to ground states of their daughter nuclides via gamma decay. In the embodiments of the present invention, gamma rays created in a pair annihilation of a positron that have been emitted through beta decay, or pair-annihilation gamma rays, are detected, and on top of that, unique gamma rays detected within a predetermined short period of time ("predetermined time" or "unique gamma ray window period," which will be mentioned later), will be used for identifying nuclides. More specifically, the unique gamma ray emitting nuclides of first and second energy values are used for the first and second probes respectively, and an arbitrary gamma ray detector that can operate measurement while resolving the first and second energy values as necessity, or energy-resolving gamma ray detector, is adopted. This makes it possible to determine as to which of the first or the second probe should be attributed for the coincidentally measured events in the group of the PET detectors. Image reconstruction processing for obtaining respective probe distribution images from the coincidentally measured events can be carried out as similarly to the conventional PET device. It should be noted in this context that both of the first and second probes may include a probe called Type-B probe, which will be described later.

In the present invention, an aspect adopting the first probe and PET probe is also provided, as mentioned above. The PET probe in this aspect is a probe labeled by a positron emitting nuclide that mainly becomes a ground state of a daughter nuclide through beta decay, or a nuclide whose states after beta decay includes, with significant probability, a ground state of a daughter nuclide. The PET probe may be one that has been used for a nuclide that is related to the emission of pair-annihilation gamma rays in conventional PET device, for example, and will be referred to as Type-A nuclide in the present application. The first probe, which has been mentioned above, emits a positron through beta decay and a unique gamma ray through gamma decay. The unique gamma rays are detected by the energy-resolving gamma ray detectors. In contrast, the PET probe in the above-mentioned aspect emits positron only. Therefore, in an aspect that adopts the first probe and the PET probe, it is possible to conduct the simultaneous imaging on multi-tracer, based on whether the energy resolving gamma ray detector has detected a gamma ray or not. The energy value of the unique gamma ray from energy-resolving gamma ray detector may be used for specific purposes later, or may not be used specifically.

In these aspects of the present invention, the coincidence measurement similar to that in the conventional PET device is made, to detect the pair-annihilation gamma rays. Also, to associate pair-annihilation gamma rays and a unique gamma ray with each other, determination is made as to whether the unique gamma ray detection and the pair-annihilation gamma rays detection occurred within a certain time difference or not. Allowable window for the time difference is set by a unique gamma ray window period, or a predetermined time, that is determined in advance in consideration of a half-life of an excited state of the daughter nuclide, or of detector's time resolution.

It follows that, "coincident," or "coincidence measurement" are not meant to define that two events occurred at a completely identical time with infinitesimal accuracy in the present application. For example, two pencils of gamma rays of the pair annihilation travel through medium or space at a speed of light respectively, and are then detected by different detectors through illumination of scintillation light, through collection of electric charge, or the like. That is, the perfect matching among detection timings cannot be assured due to various phenomena related to actual measurements, such as variation of difference in the distances between the positions of respective pair annihilations and the detectors, difference of temporal responses of the detectors. Thus, the term of coincident, or coincidence measurement in the present application does not define perfect matching in the timings. The "coincidence" in the conceptual or practical aspect of the present invention permits difference in time to a certain amount and includes a certain period of time.

In aspects of the present invention, processing of differently reconstructing images for two probes on computer may mean reconstructing at least two images separately. In an aspect adopting the first and second probes, both of which are labeled by a nuclide that emits unique gamma ray through gamma decay, typically, energy values of unique gamma rays from respective probes are identified, and images based on the pair-annihilation gamma rays from respective probes are separately reconstructed in order to distinguish respective probes. On the other hand, in an aspect adopting the first probe that emits unique gamma rays and PET probe that does not emit a unique gamma ray, images of respective probes are separately reconstructed based on, for example, whether unique gamma rays has been detected or not. It is to be noted that separately reconstructing images does not always mean reconstructing respective images that only indicate respective probes. For example, in an aspect adopting the first probe that emits a unique gamma ray and PET probe, the measurement efficiency for detecting the unique gamma ray emitted by the first probe cannot be 100% from the nature of the detection principle. This means that the pair-annihilation events that are not accompanied by coincidentally detected unique gamma ray may include ones caused by the first probe in addition to ones originating from a PET probe. Consequently, the combination of images to be reconstructed includes one image that reflects both distributions for the first and PET probes and another image that reflects distribution for the first probe.

In aspects of the present invention, computers may be included in their elements. The computers are arbitrary computing device in general having a processing unit and a memory device, in which arbitrary program operation is controlled, and resources such as memory are managed on an appropriate operating system. Moreover in aspects of the present invention various recording means may be adopted. These recording means may refer devices that are capable of recording information in memory devices in the computer and are able to distinguish pieces of information as necessity.

Advantageous Effect of the Invention

According to some aspects of the present invention, while taking advantage of such features of PET devices as superior sensitivity, quantitative performance, and resolution capability, it is possible to conduct simultaneous imaging of a plurality of probes differently with each other.

BRIEF DESCRIPTION OF THE DRAWINGS

FIG. 1a indicates a decay scheme of a positron emitting nuclide adopted for conventional PET device, or Type-A, and FIG. 1b indicates a decay scheme of a nuclide that emits a unique gamma ray adopted in embodiments of the present invention, or Type-B.

FIG. 2 is an explanatory chart of a decay scheme of Type-B nuclide that can be used in embodiments of the present invention by way of practical example.

FIG. 12a indicates an image reconstructed from the pair-annihilation gamma rays when unique gamma rays are not detected, whereas FIG. 12b indicates an image reconstructed from the pair-annihilation gamma rays when unique gamma rays are detected.

DESCRIPTION OF THE EMBODIMENT

Figure 1:
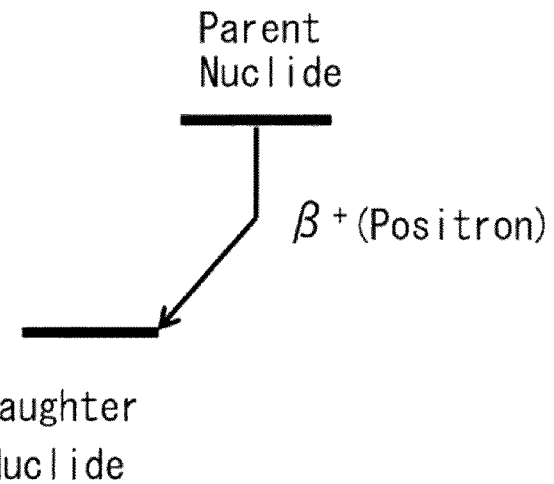
FIG. 1 is a chart indicating decay schemes of nuclides adopted in embodiments of the present invention in a pair, combined with nuclides used mainly for imaging with conventional PET device.
Figure 1:
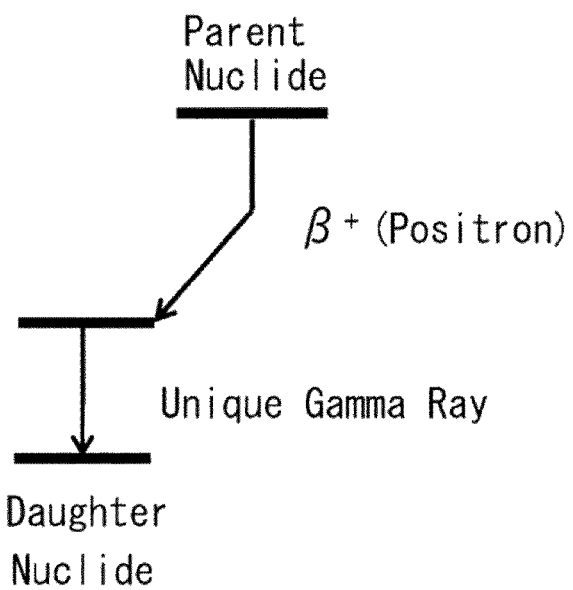

The embodiments of the invention will be described below. For all drawings, the common reference numerals are given to common part or element in this description unless otherwise noted. Moreover, each element in the drawing should be understood as not being drawn to scale.

Fundamental schemes of the embodiments are described in Fundamental Embodiment in the description, and more detailed embodiments to be practiced based on the fundamental schemes are described in Embodiments 1 and 2.

<Fundamental Embodiment>

In the Fundamental Embodiment, fundamental schemes of embodiments of the present invention will be described. The description provided in the present embodiment should be applied also to the other embodiments.

1. Fundamental Scheme 1-1. Operation Mechanism

In the embodiments of the present invention, what is adopted are positron emitting nuclides that have decay schemes different from ones for positron emitting nuclides, which have been mainly used for conventional PET device. FIG. 1 is a chart indicating decay schemes of nuclides adopted in embodiments of the present invention, in a pair with nuclides used mainly for imaging with conventional PET device. FIG. 1a indicates a decay scheme (hereinafter referred to as "Type-A") of a positron emitting nuclide adopted mainly for conventional PET device, whereas FIG. 1b indicates another decay scheme ("Type-B") of another nuclide that emits a unique gamma ray adopted in embodiments of the present invention.

As indicated in FIG. 1a, for the positron emitting nuclide of Type-A decay scheme (called "Type-A nuclide") adopted mainly for image capturing with the conventional PET device, transition of the nuclide occurs through beta decay over energy levels, from a parent nuclide before the decay to a ground state of its daughter nuclide, which is a final state after the decay. Therefore, what is emitted in the transition of the decay of Type-A nuclide is a positron only, except a neutrino. In contrast, for a nuclide of Type-B decay scheme (called Type-B nuclide) as indicated in FIG. 1b, a final state of the transition of beta decay from the parent nuclide is an excited state of its daughter nuclide. Therefore, the daughter nuclide for the Type-B after the beta decay further makes transition to its ground state accompanied by emission of a unique gamma ray of an energy value, which corresponding to the energy difference between the excited and ground states and is unique to the nuclide. The timing when the unique gamma ray is emitted by Type-B nuclides is governed by a probability explained by quantum mechanics and is dependent on the internal structure of the nucleus. A measure of the lifetime of transition from the excited state to the ground state of the daughter nuclide is given by its half-life, for example.

Figure 2A:
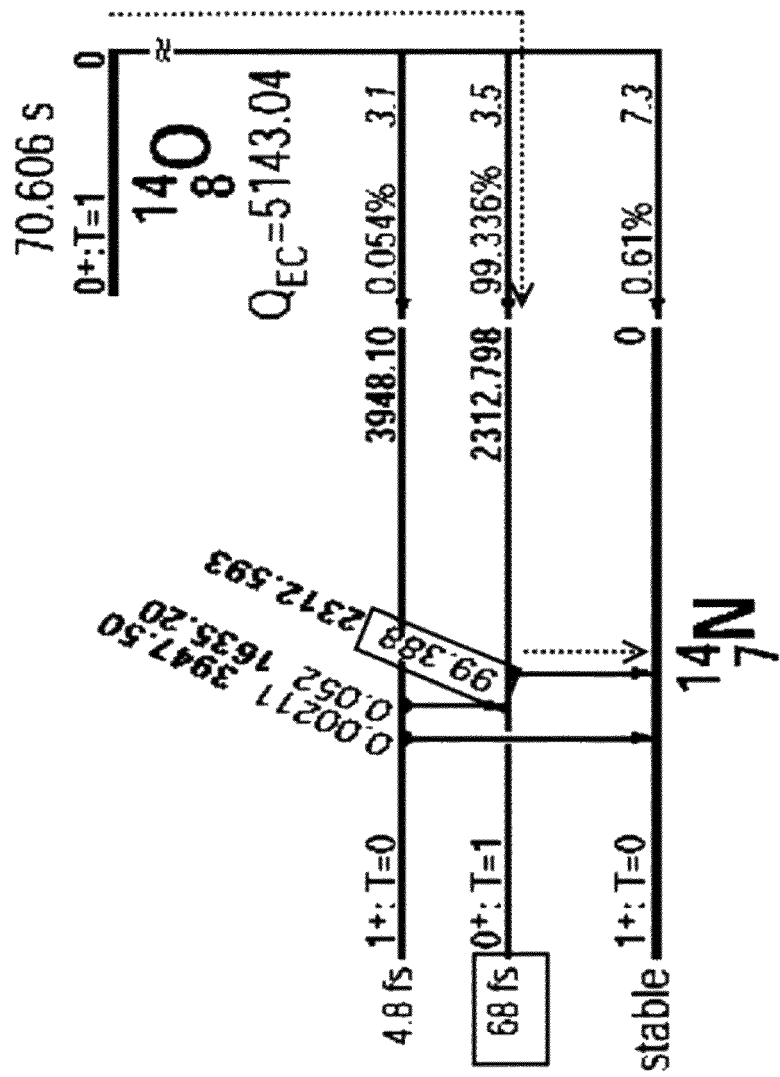
FIGS. 2a and 2b indicate decay schemes of $^{14}$O to $^{14}$N and $^{94m}$Tc to $^{94}$Mo, respectively.
Figure 2B:
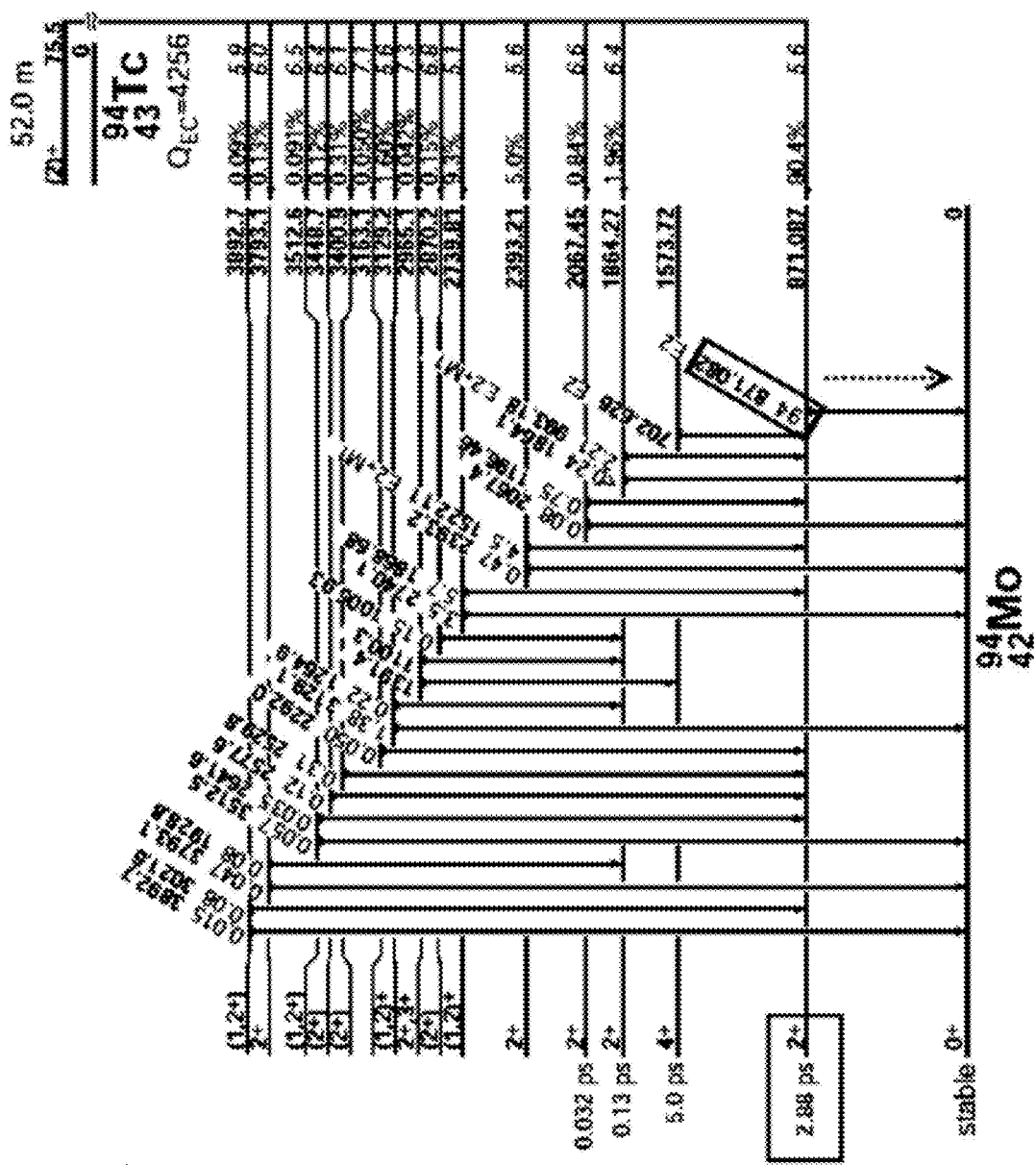

FIG. 2 is a chart indicating a decay scheme for a Type-B nuclide in FIG. 1b by way of specific example. FIG. 2a indicates a decay scheme from $^{14}$O, a parent nuclide, to $^{14}$N, its daughter nuclide. FIG. 2a depicts that, before arriving at a ground state of $^{14}$N, $^{14}$O (the parent nuclide) first makes a transition to an excited state of $^{14}$N (the daughter nuclide) with 99.4% probability, and thereafter makes another transition to a ground state of $^{14}$N while emitting a unique gamma ray of 2312 keV with half-life of 68 femtoseconds (fs). Also FIG. 2b indicates a decay scheme from $^{94m}$Tc, a parent nuclide, to $^{94}$Mo, its daughter nuclide. FIG. 2b depicts that, before arriving at a ground state of $^{94}$Mo (the daughter nuclide), $^{94m}$Tc (the parent nuclide) makes transition to an excited state with nuclear spin of 2+ of $^{94}$Mo (the daughter nuclide) via several excited states, and thereafter makes further transition to a ground state of $^{94}$Mo (the daughter nuclide) while emitting a unique gamma ray of 871.0 keV with half-life of 2.88 picoseconds (ps). The fraction of $^{94m}$Tc that follows such a decay route, or gamma ray emission ratio, is 94.2%.

It should be noted that, some nuclides conventionally used for PET probes are known to emit unique gamma rays with small probability, and thus should be classified, to be precise, as Type-B nuclides. For example, although $^{64}$Cu emits a unique gamma ray of 1346 keV with probability of 0.4%, it has been used in PET probe. However, in the description set forth in the present application, nuclides that has been conventionally used for a PET probe will be described as Type-B nuclides regardless of their unique gamma ray emitting properties, if the unique gamma rays are utilized for imaging; whereas they will be described as Type-A nuclides, if the unique gamma ray is not utilized and only the pair-annihilation gamma rays of 511 keV are used for imaging. It means that, only the Type-A nuclides whose pair-annihilation gamma rays of 511 keV are used and the unique gamma rays are not utilized, unlike the present application, may include not only those that make transition to a ground state of their daughter nuclide with 100% probability, but also those that make transition to a ground state of their daughter nuclide after beta decay with high probability. Such classification of nuclides explicitly indicates that, among nuclides conventionally used for a PET probe, nuclides having non-zero probability of unique gamma ray emission are not excluded in the embodiment.

Hereinafter, agents or probes labeled by the Type-A nuclide will be referred to as Type-A probes, whereas agents or probes labeled by the Type-B nuclide will be referred to as Type-B probes.

1-2. PET Device

Figure 3:
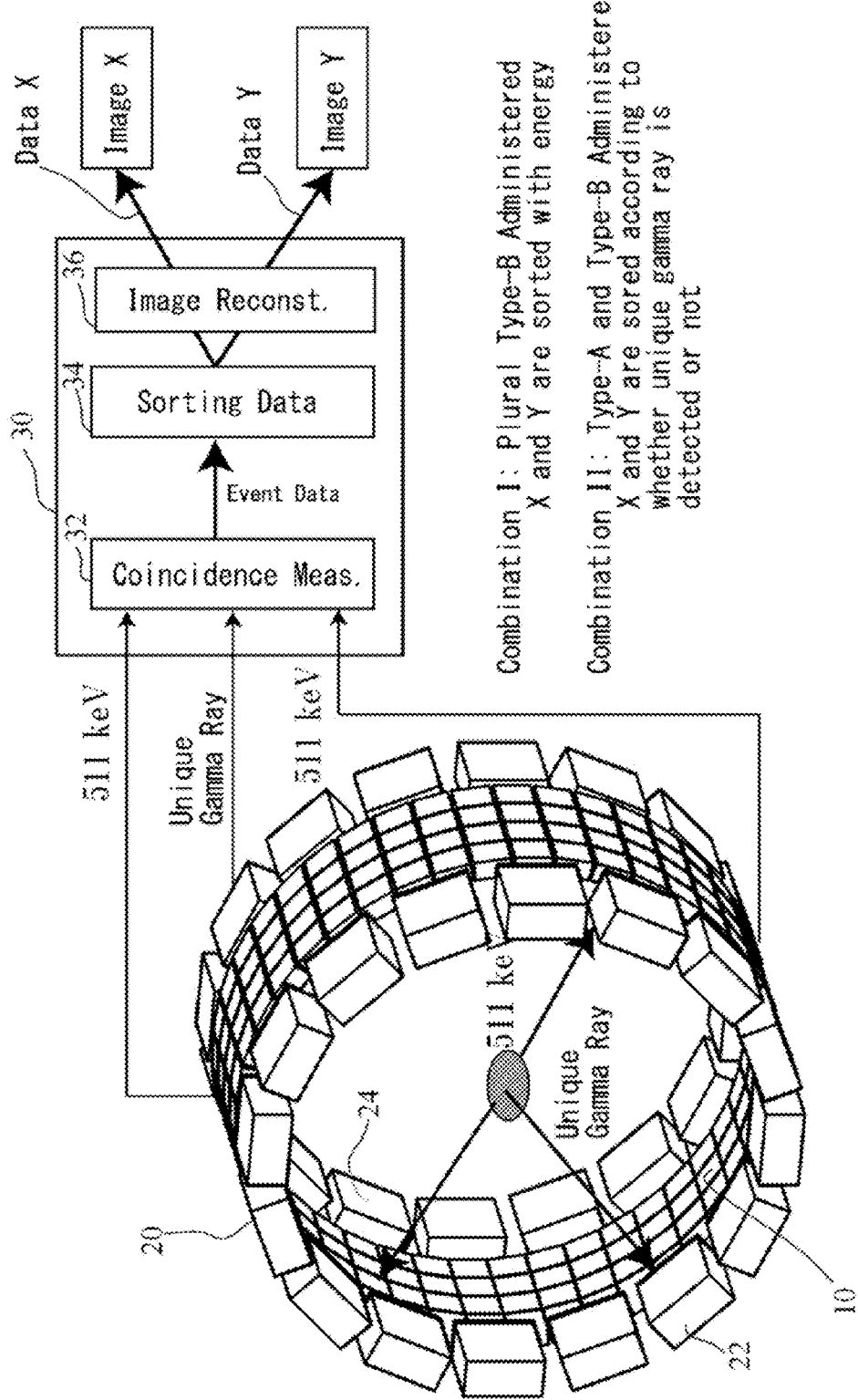
FIG. 3 is a schematic diagram of a PET device for simultaneous imaging on multi-tracer adopted in an embodiment of the present invention.

To capture distributions of a plurality of probes with a subject to be imaged to which the Type-B nuclide is administered, an improved PET device that utilizes unique gamma rays from the Type-B nuclides, or a PET device for simultaneous imaging on multi-tracer, is provided in the present embodiment. FIG. 3 is a schematic diagram of a PET device for simultaneous imaging on multi-tracer adopted in the present embodiment. The PET device for simultaneous imaging on multi-tracer 100 in the FIG. 3, or hereinafter referred to as "PET device 100," detects gamma rays pair of 511 keV that accompanies pair annihilation of a positron by using a group of PET detectors 10 disposed in a ring arrangement similar as conventional PET device. The group of PET detectors 10 may also be referred to as a group of PET gamma ray detectors. The group of PET detectors 10 includes individual PET detectors 10 that are arranged generally to form a cylindrical surface as in FIG. 3. Each of the PET detectors 10 receives gamma rays coming from inside of the cylindrical surface and outputs signals responsive to interactions with the gamma rays. In particular, the signals that are output from any two of the PET detectors 10 are called a pair-annihilation detection signal when the signals indicate that pair-annihilation gamma rays have been detected, where the pair-annihilation gamma rays were emitted into opposite directions each other due to pair annihilation of a pair of a positron and an electron. There is situated an object (not shown), such as a living body that may become a subject to be imaged, inside of the cylindrical surface. Inside the object, tracers that act as probes accumulate in various regions such as portions of the living body are distributed three dimensionally. FIG. 3, however, illustrates only a region where the Type-B probe is distributed.

When signals from respective PET detectors 10 in the PET device 100 indicate that two of the detectors have detected coincidentally gamma rays of 511 keV, it is considered that the pair annihilation has occurred somewhere on a straight line connecting the two detectors inside of the cylinder, as similarly to the conventional PET device. Therefore, the straight line along which the pair-annihilation gamma rays traveled can be estimated with the group of the PET detectors 10 as a straight line connecting positions for respective PET detectors 10 that has detected each of the pair of pair-annihilation gamma rays. As described above, the group of PET detectors 10 works as position sensitive detectors. Moreover, the pair-annihilation detection signal from the group of PET detectors 10 will be used for reconstructing images, irrespective of what sort of probes are used.

Typical PET device 100 in the present embodiment further comprises a unique gamma ray detector 20. The unique gamma ray detector 20 may be referred to as an energy-resolving gamma ray detector. In the PET device 100 of the present embodiment, the unique gamma ray detector 20 is configured as a group of the unique gamma ray detectors 20 to conform to the group of the PET detectors 10. The unique gamma ray detectors 20 may be arranged in an arbitrary region in an open space where there is no PET detector 10 for detecting pair-annihilation gamma rays. An example arrangement of the unique gamma ray detectors 20 is such that a group of many unique gamma ray detectors 20 are placed in ring shapes themselves on both sides of the group of the PET detectors 10, on a cylinder surface of coaxially aligned to a cylinder of the group of PET detectors, which are also arranged to form a ring shape, as illustrated in FIG. 3. From the unique gamma ray detectors 20, pulse height signals that reflect energy values of gamma rays will be obtained. Thus, the pair-annihilation detection signal contains information of timing as to when the unique gamma ray has arrived and information with respect to energy of the unique gamma ray.

A PET device having the same functions of the PET device 100 may be manufactured by modifying a conventional PET device that is equipped with similar detectors as the PET detectors 10. In such a case, arbitrary gamma ray detector that can measure energy is added to a position where operation of the already existing PET detectors are not affected, as similarly to the group of unique gamma ray detectors 20 in the PET device 100 as an example. The PET device made by adding the unique gamma ray detector to the conventional PET detector is advantageous because it can provide simultaneous imaging on multi-tracer while minimizing structural modification to the conventional PET device.

The function required for the unique gamma ray detectors 20 when operating the PET device 100 is to measure the energy of the unique gamma ray and to determine the detection timing thereof; thus position sensitivity is not necessary. Also, the type of the gamma ray detectors that can be adopted as the unique gamma ray detectors 20 is not specifically limited. For example, a scintillation detector having such scintillator as NaI, BGO, LSO, LaBr, or the like, and a semiconductor detector having such semiconducting material as Si, Ge, CdTe, CdZnTe or the like, may be adopted for the unique gamma ray detector 20.

It should be noted that since position sensitivity is not required for the unique gamma ray detectors 20, it is not necessary to provide the unique gamma ray detectors in a group. In spite of this, the unique gamma ray detectors 20 of a number of detectors forming a group are provided to have a favorable counting rate for the device as a whole without reducing the total solid angle viewed from the subject to be imaged. That is, although it depends on size of the unique gamma ray detectors 20 or amount of gamma ray dose to be measured, the counting rate per one unique gamma ray detector 20 may become too high. In such a case, to reduce the counting rate at each unique gamma ray detector 20 to a favorable level, dividing the size of the unique gamma ray detectors 20 into an appropriate size and combining a plurality of the reduced ones may be effective.

1-3. Imaging Processing

As indicated in FIG. 3, the PET device 100 in embodiments of the present invention comprises imaging processor 30. The imaging processor 30 further comprises coincidence determination unit 32 that executes coincidence measurement on the received signal and outputs the event data. The imaging processor 30 further comprises data sorting unit 34 that sorts the event data from the coincidence determination unit 32 by data of unique gamma rays and outputs the sorted data. And the imaging processor 30 further comprises image reconstructing unit 36 that reconstructs images using data from the data sorting unit 34.

In the conventional PET device, determination is made as to whether the detected gamma ray has been produced by a single pair annihilation event or not, by using signals from each detectors in the group of the PET detectors. In contrast, in imaging processor 30 in embodiments of the present invention, determination as for the coincidence measurement is made by using signals from the unique gamma ray detectors 20, as well as a signal ("pair-annihilation detection signal") that has been identified as related signals to pair-annihilation gamma rays among signals from respective PET detectors 10. That is, the determination is made not only as to whether the detected gamma ray has been produced by a single pair annihilation event or not, but also as to whether the pair annihilation event has been accompanied by the detection of a unique gamma ray or not. Consequently, in the PET device 100, the type of the nuclide, or the probe, can be identified, which would have been impossible only with the pair-annihilation detection signal.

Figure 4:
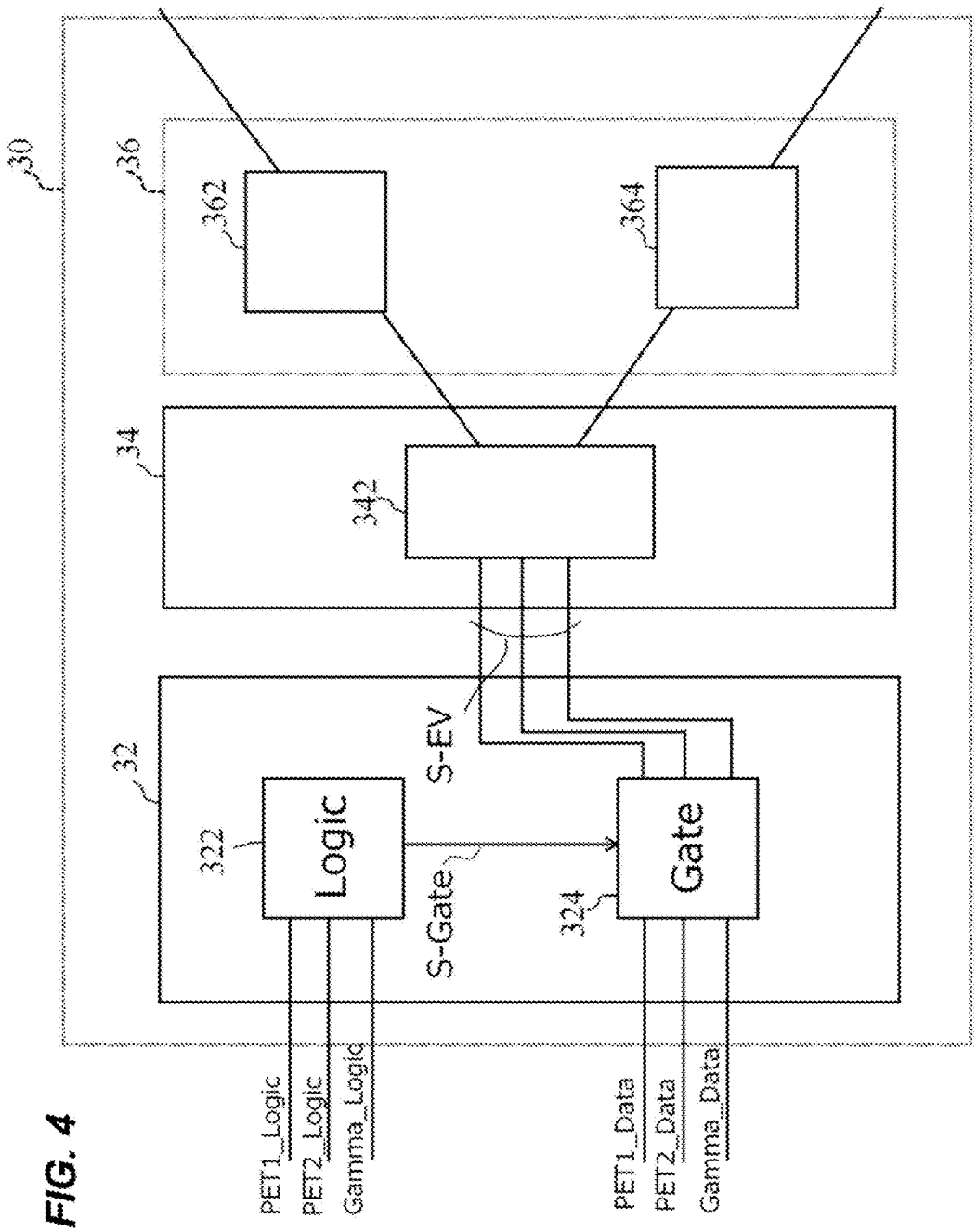
FIG. 4 is a block diagram of a signal processing scheme of an imaging processor in a PET device for simultaneous imaging on multi-tracer adopted in an embodiment of the present invention.

The imaging processor 30 of the PET device 100 conducts the operation mentioned above through either the hardware processing or software processing. Regarding the case when the aforementioned processing is implemented with hardware, the circuit structure will be further described with reference to the block diagram of the imaging processor 30 in FIG. 4. FIG. 4 is a block diagram of an example scheme for hardware processing of an imaging processor 30 in the PET device for simultaneous imaging on multi-tracer adopted in the present embodiment. The coincidence determination unit 32 in the imaging processor 30 executes coincident determination on signals received from the PET detectors 10. In FIG. 4, each signal from each PET detector 10 is divided into a signal for indicating timing of detection of the gamma ray at the PET detector 10, and another signal for indicating both position and energy of detected gamma ray, by a part of the imaging processor 30, or by a hardware processing circuit of publicly known (not shown). Thereafter, the signal indicating the timing of detection of the gamma ray at the PET detector 10 and the signal for indicating both position and energy of the detected gamma ray are input to the coincidence determination unit 32. FIG. 4 depicts signals PET1_Logic and PET2_Logic for indicating the timings of detection of the gamma rays and signals PET1_Data and PET2_Data for indicating detected positions and energy values of the gamma rays. In the PET detectors 10, a signal regarding detection of one of pair-annihilation gamma rays is divided into a signal PET1_Logic and a signal PET1_Data, and another signal regarding detection of the other of the pair-annihilation gamma rays is divided into the signal PET2_Logic and the signal PET2_Data. Thus, the pair-annihilation detection signal comprises the signal PET1_Logic and the signal PET1_Data, and the signal PET2_Logic and the signal PET2_Data.

The signal from the unique gamma ray detector 20 is also divided into a signal Gamma_Logic for indicating timing of detection of gamma ray at the unique gamma ray detector 20 and another signal Gamma_Data for indicating energy value of the detected gamma ray, and input into the coincidence determination unit 32.

The coincidence determination unit 32 is described in detail based on functions therein. It comprises a logic unit 322 for determining the timing and generating a gate control signal S-GATE that indicates whether a coincidence measurement has occurred, and a gate unit 324 for executing gating processing to output an event data signal S-EV based on the gate control signal S-GATE from the logic unit 322. The event data signal S-EV is then input to a logic unit 342 of the data sorting unit 34, and the logic unit 342 outputs data for reconstructing images according to a predetermined sorting logic. Upon reception of the data, the image reconstructing unit 36 that receives each piece of data then executes image reconstruction processing by using separate image reconstructing processors 362 and 364. Through the processing as described above, separate images are reconstructed from the sorted data. More detailed structure of the data sorting unit 34 in line with identification processing of probes will be described specifically in section 2-4 titled "Imaging Processor Suitable for Type-Combinations of Detectors."

1-3-1. Image Reconstruction Processing

The sorted pieces of data are processed similarly as data in conventional PET device at the image reconstructing processors 362 and 364. For example, the reconstruction can be executed by well-known methods, such as, "FBP (Filtered Back-Projection) method," "OS-EM (Ordered Subset ML-EL) method," or "MAP-EM (Maximum a Posterior-EM) method." These methods are described in Non-Patent Document 2, as an example.

1-4. Implementation of Imaging Processor

In the above description, the processing in hardware is described for the purpose of a clear explanation. However, as is evident for the skilled in the art, the present embodiment can be practiced in various implementations. For example, the processing in data sorting unit 34 can be executed through software on a computer rather than processing in hardware. Moreover, especially when a data acquisition circuit capable of capturing signals with minimal dead time is used, the processing in the coincidence determination unit 32 also can be executed through software on a computer. Although the structure of the imaging processor 30 indicated in FIG. 4 is provided in an organized manner to describe consistently with FIG. 3, the processing in the imaging processor 30 in FIG. 3 can be substantially practiced in another implementation. For example, the processing with hardware in AND gate G2 can be executed as a part of logical processing in the logic unit 342. That is, the imaging processor 30 in the PET device for simultaneous imaging on multi-tracer adopted in the present embodiment receives signals from the group of the imaging processor 30 and identifies which pair of PET detectors has actually captured the pair-annihilation gamma rays of 511 keV with the coincidence measurement. Then the imaging processor 30 utilizes the detection of the gamma rays related to the pair annihilation to reconstruct images based on the pair-annihilation gamma rays.

The image processor, which may be implemented in a circuit as hardware and in processing on a computer in software, is configured as follows.

For implementing in the hardware with an electronic circuit, signal paths for timing are provided with respect to each signal from the PET detectors 10 and unique gamma ray detector 20 are configured, and coincidence measurement logic or a circuit to determine a hit pattern in the detectors is implemented. Also, to utilize energy signal from the PET detectors 10 or the unique gamma ray detector 20, signal paths for amplitude are provided, and data for reconstructing images are obtained from an electrical signal via a shaping amplifier and an analog-to-digital converter, for example.

On the other hand, for implementing in the software for the coincidence measurement on a computer, temporal information, or timestamp, is recorded in the event data from respective detectors, and the coincidence measurement is executed later. Such scheme is also a part of the present embodiment.

Figure 5:
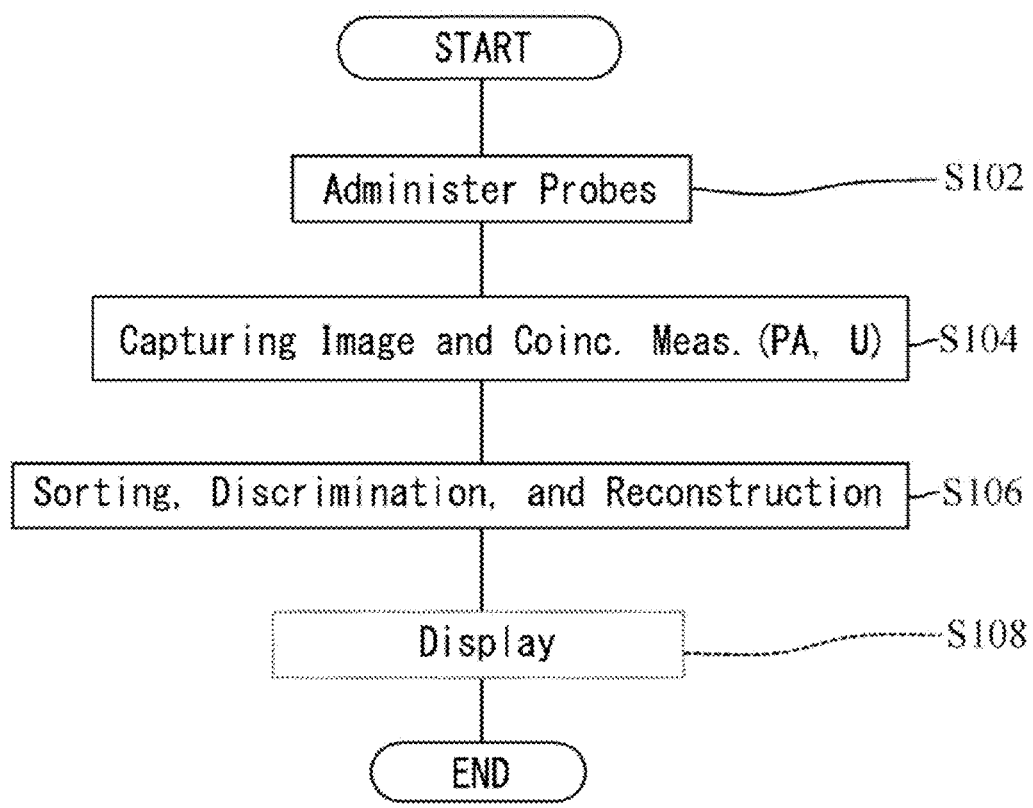
FIG. 5 is a flow chart indicating processing of a method for imaging with a PET device for simultaneous imaging on multi-tracer adopted in an embodiment of the present invention.

FIG. 5 is a flow chart indicating processing of a method for imaging with a PET device 100 in the present embodiment. In the PET device 100 of the present embodiment, the probes are administered to the subject to be imaged (S102). At least one of the probes has been labeled by a nuclide that emits a unique gamma ray following the positron emission (Type-B nuclide).

Then, image capturing and coincidence measurement are conducted (S104). The coincidence measurement is to determine events with the group of the PET detectors 10 and the unique gamma ray detector 20, which is carried out in parallel with the image capturing. The coincidence measurement to determine the pair-annihilation gamma ray is the same as one in the conventional PET device. Also, to determine whether the nuclei that generated the pair-annihilation gamma rays also emitted the unique gamma ray, determination is made as to whether the unique gamma ray has been detected coincidentally with the detection of the pair-annihilation gamma rays.

Moreover, the sorting of the event data is carried out according to the energy of the unique gamma rays or according to whether there have been the detection or not, and then images for respective sorted data are reconstructed (S106).

Thereafter, the PET device 100 having the structure and functions mentioned above presents images that have been separately reconstructed on arbitrary display device, not shown, in a manner respective images can be distinguished with each other (S108).

By providing the PET device having the structure and functions mentioned above, the simultaneous imaging on multi-tracer can be practiced in a manner a plurality of probes are imaged differently while taking advantages of the high spatial resolution and superior quantitative performance, both of which have been the advantages in the conventional PET device.

1-5. Combination of Probes

Descriptions will be given to combinations of probes that can be distinguished through the PET device 100 when they are administered simultaneously to a subject to be imaged. Typically, such combinations are explained by the following general classification.

Combination I: a plurality Type-B probes is used, where respective Type-B probes emit respective unique gamma rays having different energy values each other.

Combination II: a combination of Type-A and Type-B probes are used.

The determination regarding which probe is relevant to the measured pair-annihilation signal (hereinafter called "probe identification") may be performed, in the case of Combination I indicated above, by detecting energy values of detected unique gamma rays. The probe identification in the case of Combination II may be performed not only based on whether a unique gamma ray has been detected or not, but also using energy values of the unique gamma ray in the identification, while suppressing noise in the image. Brief annotations for the difference between Combinations I and II are indicated in FIG. 3. Thus, the imaging processor 30 executes sorting the event data originating from the pair-annihilation determination signal by the energy value of the gamma ray (for Combinations I and II), and based on the existence of the gamma ray (for Combination II). Such a sorting processing may be executed, for Combination I, by use of an energy value measured by the unique gamma ray detector 20, as well as its coincidence with the pair-annihilation gamma rays. On the other hand, for Combination II, it may be executed according to whether the unique gamma ray measured by the unique gamma ray detector 20 has been measured coincidentally with the pair-annihilation gamma rays, and discrimination of the unique gamma ray energy from 511 keV. It should be noted that the present embodiment includes a combined set of Combinations I and II, which is realized when three types or more probes are administered.

2. Details of PET Device

In what follows, description will be made for the details of the PET device provided in the present embodiment.

2-1. Detector Functions as PET Device

The PET device of the present embodiment is typically has a structure of the PET device 100 described above. However, similar functions to that of the PET device of the present embodiment can be realized by modifying the operation of the PET detectors in the conventional PET device that have been manufactured for detecting the pair-annihilation gamma rays of 511 keV, in such a manner they serve the same function as the unique gamma ray detector 20 as well. In such modifications of the conventional PET device, the PET detectors provided in the device have both functions of "PET gamma ray detectors" and "energy-resolving gamma ray detectors" at a time. Also the PET device being qualified as the present embodiment in such a case is not required to have "PET gamma ray detectors" and "energy-resolving gamma ray detectors" separately.

2-1-1. Dedicated and Dual-Use Operations

In view of the functions of the PET detectors for pair-annihilation gamma rays, detector structures that can be selected optionally are summarized as follows. Specifically, by focusing on the operation of the PET detectors, the operations of the PET device in the present embodiment can be classified into: an operation in which no detector in the group of the PET detectors detects a unique gamma ray (hereinafter referred to as "dedicated operation"), and another operation in which at least one detector of the group of the PET detectors detects a unique gamma ray ("dual-use operation"). In dedicated operation, a unique gamma ray detector separate from the PET detector is required to detect the unique gamma ray. In contrast, a unique gamma ray detector is not always required in the PET device, in the dual-use operation.

2-2. Particular Types of Detectors

The combination of the PET detectors and the unique gamma ray detector used in the PET device of the present embodiment will be described. Gamma ray detectors are generally classified into scintillation detectors using scintillator material, and semiconductor detectors using semiconducting material. For the PET detectors and the unique gamma ray detector in the present embodiment such scintillation and semiconductor detectors can also be adopted. Concepts as for the appropriate detector selection will be described in terms of the performances of the detectors especially for detecting the unique gamma ray.

Selection of the detectors can be made in consideration of performance, such as energy resolution, temporal resolution, counting tolerance, and sensitivity, as well as in consideration of costs. The energy resolution means whether sufficient accuracy is achieved for measuring with resolving energy values among unique gamma rays, or between the unique gamma ray and the pair-annihilation gamma rays. The counting tolerance is an upper limit of the number of detection of the gamma ray per a unit time period. And the sensitivity is a ratio of the number of detection out of a total number of unique gamma rays emitted by the subject to be imaged.

To present a typical fundamental scheme in the PET device 100 indicated in FIG. 3, description is made assuming the dedicated operation is carried out while both the PET detectors 10 and the unique gamma ray detectors 20 are equipped. When practicing the present embodiment, the dual-use operation can also be adopted for the PET device 100 in FIG. 3. Moreover, valuation for types of the detectors when choosing the detector may be different between the dedicate operation and the dual-use operation mentioned above.

The evaluation of the scintillation detectors and the semiconductor detectors are summarized for the dedicated operation in Table 1, and for the dual-use operation in Table 2.

TABLE 1

| PET | γ | |
| --- | --- | --- |
|  | Scintillator | Semiconductor |
| Scintillator | 3/1/2/1 | 1/3/2/3 |
| Semiconductor | 3/1/2/3 | 1/3/2/3 |

TABLE 2

| PET | γ | | |
| --- | --- | --- | --- |
|  | None | Scintillator | Semiconductor |
| Scintillator | 3/1/3/1 | 3/1/1/1 | 2/2/1/2 |
| Semiconductor | 1/3/3/1 | 2/2/1/2 | 1/3/1/3 |

Cells in Tables 1 and 2 indicate evaluations for type of the unique gamma ray detector 20 in columns and type of the PET detectors 10 in lines. For example, lower left cell in Table 1 shows the evaluation for choices of scintillation detector as the unique gamma ray detector 20 and semiconductor detector as the PET detectors 10. In Table 2, the left column is provided for cases when the unique gamma ray detector 20 is not used. The other columns in the Table 2 are provided for cases when the unique gamma ray detector is used while being operated with the dual-use operation.

In each cell of the tables, what is indicated are the results for four evaluation items separated by slash or "/". That is, energy resolution, counting tolerance, sensitivity, and cost are combined and indicated based on the inventors' understandings. The numerals 1, 2, and 3 respectively are symbols representing the inventors' understandings, for "excellent," "sufficient," and "insufficient" in this order.

It should be noted that these evaluation results are described for the purpose of explaining the features of the present embodiment only. That is, even "3 (insufficient)" is indicated for the evaluation; it does not mean that the combination cannot be adopted in the PET device for the embodiments of the present invention. Moreover, the performance depends on the materials of the scintillator and the semiconductor, thus the respective evaluations may vary accordingly. In addition, in the course of the development of the technology respective evaluations may also be changed. For example, although the scintillation detectors using NaI, BGO, LSO or the like are low cost detectors, their energy resolution is relatively lower than ones for the semiconductor detectors in general. Compared with the above, although the semiconductor detectors using Si, Ge, CdTe or the like are costly detectors, they show high energy resolution. However, such scintillators as LaBr, which have been common these days, have relatively high energy resolution, and are preferably adopted for the PET detectors or the unique gamma ray detectors in the present embodiment. This shows that the evaluations provided in the Tables 1 and 2 in the above, are merely evaluations in general for the types of the detectors for the time being.

Six typical combinations of these types of detectors, or type-combinations are further described in detail. Two type-combinations of them are used only for the dual-use operation, whereas the remaining four type-combinations may be used for both of the dual-use and dedicated operations. As for the PET for clinical use, the general PET detectors described here does not mean a whole body type, but a partial capturing type, including one that captures whole body image by moving scanning.

2-2-1. Detectors Type-Combination 1

First type-combination of the detectors, which corresponds to upper left cell in Table 2, is one that will be used for triple fold coincidence measurement only with the PET device having scintillation detectors. That is, the pair-annihilation gamma rays and the unique gamma ray are detected by the scintillation detectors in the PET device. The most common general PET device of these days uses scintillation detectors having NaI, BGO, LSO or the like for detecting gamma rays. These scintillation detectors have energy resolution of around several ten keV—several hundred keV. Therefore, without changing the detectors in the conventional PET device, dual-use operation of coincidence measurement among two pencils of pair-annihilation gamma rays and a pencil of a unique gamma ray, or triple fold coincidence measurement, is possible by changing hardware processing or downstream processing in the image processing and so forth, while keeping the structure of the conventional PET device. In this type-combination of detectors, the detectors may be identical to those in the conventional PET device, which means there would be no need for significant additional cost for production compared with the conventional PET device.

However, the energy resolution of the scintillation detectors used for detecting the unique gamma ray is not so high, or around several ten keV—several hundred keV as described above. Therefore, energy of the unique gamma ray from the Type-B probe must differ from the energy of the pair-annihilation gamma ray (511 keV) far more than the resolution. In addition, if the scintillation detectors in the conventional PET device are used without modification, the solid angle formed at the subject to be imaged by the scintillation detectors is so small that the detection sensitivity may be low. In particular, since the scintillation detectors in the PET device are generally configured to detect the 511 keV gamma rays, it may be possible that the stopping power against the unique gamma rays with higher energy becomes insufficient.

2-2-2. Detectors Type-Combination 2

Second type-combination of detectors for practicing the present embodiment is a PET device having semiconductor detectors configured to have a unique gamma ray detector, and a signal processing system that can handle triple fold coincidence measurement, without changing the existing detectors configuration. This type-combination corresponds to lower left cell in Table 2 and may be regarded as first type-combination of detectors mentioned above while replacing the scintillation detectors by semiconductor detectors. PET imaging devices with the semiconductor detectors have been practiced recently, thus the present embodiment can be practiced without changing the detectors configuration in such PET devices. In this case, the image processing part is made in such a manner that the obtained data is classified based on whether there is a unique gamma ray or not, or on the energy value, and the classified data is used differently for respective imaging. The second type-combination of detectors has high energy resolution semiconductor detectors; thus the second type-combination has superior identification capability between 511 keV gamma ray of the positron pair annihilation and unique gamma ray, or superior discrimination capability among unique gamma rays having different energy values, to the first type-combination of detectors. It should be noted that the second type-combination of detectors has limited sensitivity of the unique gamma rays similarly as the first type-combination of detectors.

2-2-3. Detectors Type-Combination 3

Third type-combination of detectors for practicing the present embodiment is configured as a common PET device having scintillator detectors and additional scintillation detector for detecting a unique gamma ray. This type-combination corresponds to upper left cell in Table 1 and upper center column cell in Table 2. The third type-combination of detectors has lesser energy resolution in comparison with fourth type-combination of detectors having semiconductor detectors, which will be described below, because it has scintillation detectors. However, the third type-combination of detectors is advantageous because it can cover a greater solid angle with relatively less cost. The unique gamma ray detector in this case does not need any information of the gamma ray detection position, thus the positional response is not required for the additional scintillation detector. As a result, there is no need for the scintillation detector as the additional unique gamma ray detector to be sectioned into pieces like PET detectors that use positional information. Thus, the number of channels for the unique gamma ray detector may be small, and the signal processing system therefrom may be relatively simple.

It is preferable to use such scintillator with relatively high energy resolution as LaBr or the like for the additional detector, because energy identification of the unique gamma rays is conducted with it. When such scintillator is adopted, it is possible to discriminate a unique gamma ray having closer energy to 511 keV, and to discriminate a plurality of unique gamma rays having closer energy values with each other.

2-2-4. Detectors Type-Combination 4

Fourth type-combination of detectors for practicing the present embodiment is one with semiconductor detectors such as Ge, Si, and CdTe detectors for unique gamma rays, in addition to scintillation detectors in the PET device. This corresponds to upper right cells in Tables 1 and 2. Semiconductor detectors usually have higher energy resolution than scintillators. Thus, when the unique gamma ray is detected with the semiconductor detectors, high discrimination capability between 511 keV gamma rays and the unique gamma ray is achieved, which allows wide selection for the nuclides. In particular when the energy of the unique gamma rays is smaller than 511 keV, in which discrimination is required from scattered gamma rays of 511 keV, the high energy resolution is advantageous in this respect. Also in this case, there is no need for the additional detector to have positional response, similarly as the case for the third type-combination of the detectors.

2-2-5. Detectors Type-Combination 5

Fifth type-combination of detectors for practicing the present embodiment is one with a scintillation detector for the unique gamma ray detector, in addition to the PET device with semiconductor detectors. This type-combination corresponds to lower center column cell in Table 2. The detection of the unique gamma ray therefrom has similar properties with that in the type-combination 3.

2-2-6. Detectors Type-Combination 6

Sixth type-combination of detectors for practicing the present embodiment is one with a semiconductor detector for the unique gamma ray detector, in addition to the PET device with semiconductor detectors. This type-combination corresponds to lower right cell in Table 2. The detection of the unique gamma ray therefrom has similar properties with that in the type-combination 3.

2-3. Arrangement and Structure of Unique Gamma Ray Detector

In the type-combinations 3-6 in the combinations for detectors described above, the unique gamma ray detector 20 separate from PET detector 10 is adopted. In such a case, in principle there is no specific restriction on the spatial arrangement for the unique gamma ray detector 20. In other words, the unique gamma ray detector 20 may be spatially arranged arbitrarily, as long as it can detect gamma rays emitted by the Type-B probe. The ring shape arrangement as indicated in FIG. 3 is an example arrangement of positions for the unique gamma ray detector 20. The inventors have confirmed through simulation with numerical calculation, which will be described later, that such a ring shape arrangement enables detection of the unique gamma rays with a percentage sufficient for the purpose of the present invention. Thus the arrangement of the unique gamma ray detector 20 as depicted in FIG. 3 is an example one with which the simultaneous imaging on multi-tracers by use of Type-B probe is practiced with sufficient efficiency.

Also, it is possible to make various improvements on the arrangement of the unique gamma ray detector 20. For example, by shielding gamma rays that may affect measurement with the unique gamma ray detector 20, the counting rate of the unique gamma ray detectors can be suppressed. In particular, when the subject to be imaged sticks out from FOV (field-of-view), which is defined as a range where image capturing is possible by the PET device, the unique gamma ray and the pair-annihilation gamma rays come from the part of the subject to be imaged situated outside of the FOV. Such gamma rays may be useless ones for the measurement inside the FOV and raise the count rate, which may unnecessarily boost the chance of unsuccessful measurement of the unique gamma ray of interest, or which may reduce the counting limit with regard to the administered radioactivity. In such a case providing the shield for screening gamma rays from outside of the FOV at appropriate position around the unique gamma ray detector 20, such as the outer surface 22 or 24 in FIG. 3, is effective for reducing the counting rate. Example material suitable for such shields is lead or tungsten, for their large atomic number gives significant stopping power to the gamma rays.

2-4. Imaging Processor Suitable for Type-Combinations of Detectors

The imaging processor 30 indicated in FIGS. 3 and 4 for a fundamental scheme processes signals from the unique gamma ray detector for the coincidence measurement, in addition to detection of the pair-annihilation gamma rays as in the coincidence determination part in the conventional PET device. The signals from detectors used to determine whether the coincidence measurement actually occurred or not are modified to fit the type-combinations 1-6. Moreover, the operation of the imaging processor 32 (FIG. 3) with respect to the coincidence measurement, or operation and specific structure of the logic unit 322 and the gate unit 324, may be dependent upon whether the operation assumes Combination I in which a plurality of Type-B probes are administered, or Combination II in which Type-A and Type-B probes are combined and administered. Furthermore, the signals used in the imaging processor 30 for distinguishing these probes are dependent upon whether the operation is the dedicated operation or the dual-use operation. Specifically, the pair annihilation signals from the group of PET detectors 10 and the signal from the unique gamma ray detector 20 are utilized for the dedicated operation. In contrast, what are utilize for the dual-use operation are the pair annihilation signals from the group of PET detectors 10 and any signals from any detectors other than those that have actually detected the pair-annihilation gamma rays in the group of the PET detectors 10. In what follows, in the first place, operation details of the imaging processor 30 (FIG. 4) of the dedicated operation will be described separately for Combination I or a plurality of Type-B probes are administered, and for Combination II or the combination of Type-A and Type-B probes are administered. Thereafter, the case for the dual-use operation will be described.

Figure 6:
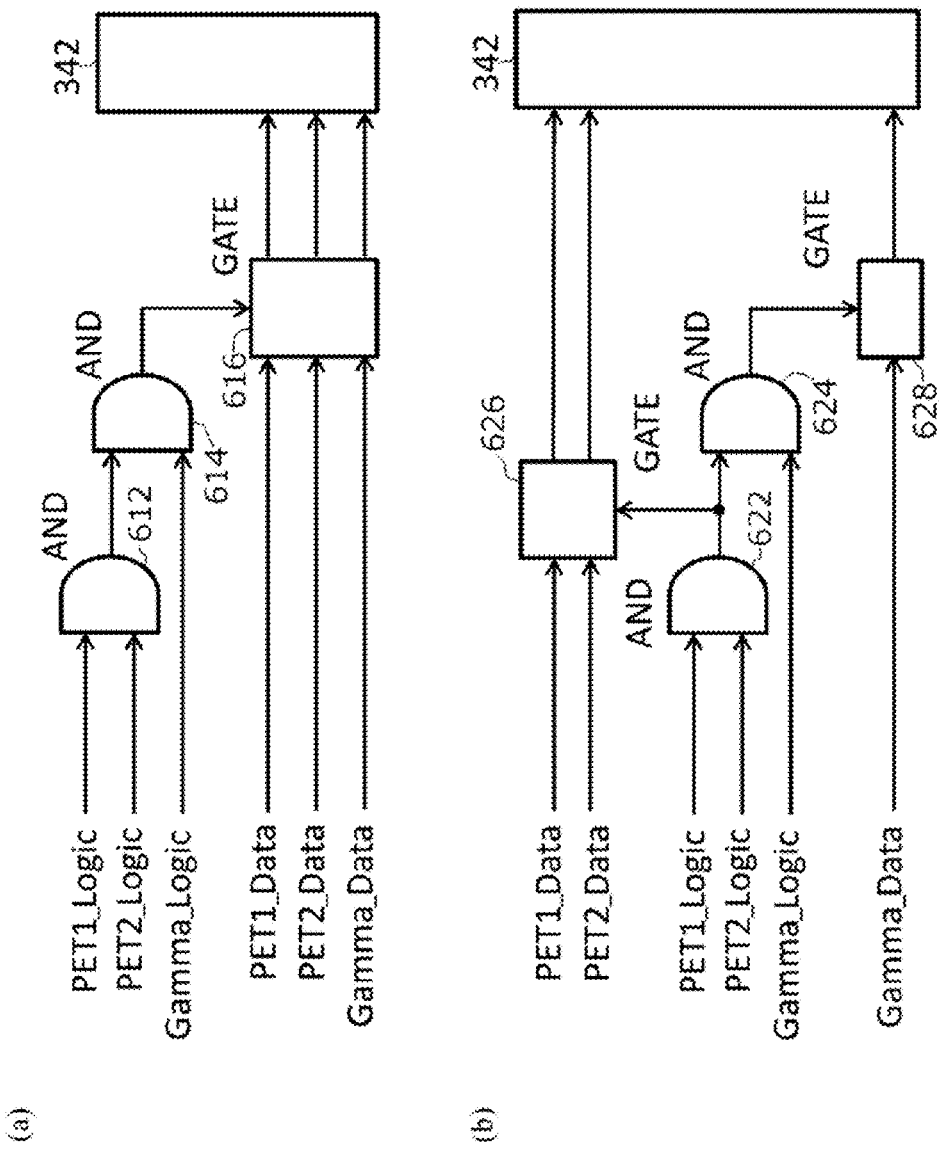
FIG. 6 is a block diagram of a detailed signal processing scheme of an imaging processor in a PET device for simultaneous imaging on multi-tracer adopted in an embodiment of the present invention.

FIG. 6 is a block diagram of a detailed processing scheme of hardware in an imaging processor in a PET device for simultaneous imaging on multi-tracer adopted in the present embodiment. FIGS. 6a and 6b indicate hardware processing operated in the imaging processor 30 in the dedicated operations respectively for Combination I in which a plurality of Type-B probes are administered, and for Combination II in which Type-A and Type-B probes are combined.

Firstly operations common to Combinations I and II will be described. In the dedicated operation, the unique gamma ray in the unique gamma ray detector 20 together with its energy is measured, and the signal from the unique gamma ray detector 20 is received by the imaging processor 30. Although in PET device 100 depicted in FIG. 3 the unique gamma ray detector 20 includes a large number of unique gamma ray detector 20, description is provided based on a signal that indicates the detection in one of the unique gamma ray detectors 20. As mentioned above, the signals PET1_Logic and PET2_Logic indicating timings of the detection of the pair-annihilation gamma rays and signals PET1_Data and PET2_Data indicating positions of the pair-annihilation and energy values of the gamma rays are produced from signals of PET detectors 10 in the signal received by the imaging processor 30 by hardware processing system (not shown) heretofore known. From signals of the unique gamma ray detector 20, a signal Gamma_Logic indicating timing of the detection of the gamma ray at the unique gamma ray detector 20, and a signal Gamma_Data indicating energy value of the unique gamma ray are generated.

Next, description will be made specifically for the case of Combination I. In Combination I indicated in FIG. 6a, where a plurality of Type-B probes are administered, signals PET1_Logic and PET2_Logic from the PET detectors 10 are input to AND 612, and the output from the AND 612 and signal Gamma_Logic are input to AND 614. The output of the AND 614 is then input to Gate 616 for controlling whether signals Gamma_Data, PET1_Data, and PET2_Data are output or not. As a result, gate 616 outputs signals Gamma_Data, PET1_Data, and PET2_Data, only when signals PET1_Logic and PET2_Logic are both asserted according to detection of pair annihilation, and, at the same time, a signal Gamma_Logic is asserted according to detection of a unique gamma ray. The logic unit 342 that receives the signals carries out sorting of signals PET1_Data and PET2_Data that are obtained through coincidence detection with signal Gamma_Data, by energy of unique gamma ray in the signal Gamma_Data, which is output by gate 616 only when the pair-annihilation gamma rays and the unique gamma ray are measured coincidentally. Therefore, the logic unit 322 is comprised of the AND 612 and the AND 614, and the gate unit 324 is comprised of the gate 616. Also the output of the AND 614 acts as the gate control signal S-GATE.

In contrast, Combination II indicated in FIG. 6b, or a case when Type-A and Type-B probes are administered, signals PET1_Logic and PET2_Logic from the PET detectors 10 are input to AND 622, then the output of AND 622 and the signal Gamma_Logic are input to AND 624. A gate 626 controls whether the signals PET1_Data and PET2_Data should be output to the logic unit 342 or not, based on output of the AND 622. In contrast, gate 628 controls whether the signal Gamma_Data should be output to the logic unit 342 or not, based on output of the AND 624. Therefore, a signal Gamma_Data is output to the logic unit 342 only when signals PET1_Logic and PET2_Logic are both asserted according to the detection of pair annihilation, and, at the same time, the signal Gamma_Logic is asserted according to the detection of a unique gamma ray, similarly as the case of Combination I in FIG. 6a. However, in this case, the signals PET1_Data and PET2_Data are output to the logic unit 342 when signals PET1_Logic and Pet2_Logic are both asserted according to detection of pair annihilation, without any connection with the signal Gamma_Logic. The logic unit 342 that has received the signals then monitors whether there is a signal Gamma_Data accompanying the unique gamma rays or not, or whether there is energy of the unique gamma rays included in the signal Gamma_Data, for conducting sorting of signals PET1_data and PET2_Data received via gate 626. Therefore, the logic unit 322 is comprised of the AND 622 and the AND 624, and the gate unit 324 is comprised of gate 626 and Gate 628. Also the outputs of the AND 622 and the AND 624 act as the gate control signal S-GATE.

Based on the operation mentioned above, detailed hardware processing for the Combinations I and II in the dedicated operation is practiced.

It should be noted that, for the purpose of sorting processing in the logic unit 342, an energy value of unique gamma ray is used in Combination I. The energy value of the gamma ray is included in the signal Gamma_Data in the output of the gate 616 indicated in FIG. 6a. In contrast, in Combination II, what is used in the logic unit 342 is whether there is found a gamma ray or not at the unique gamma ray detector, or an energy value of the gamma ray. The detection of the unique gamma ray can be specified easily based on whether there is a signal Gamma_Data or not in the output from the gate 628 in FIG. 6a.

Next, hardware processing of the dual-use operation will be described based on the description for the dedicated operation. Also, almost the same hardware processing is carried out as described with reference to FIGS. 6a and 6b in the dual-use operation. The difference regarding hardware processing between the dedicated and the dual-use operations is found in the difference of signals to be used in the imaging processor 30 for operation as described above. More specifically, the signals Gamma_Logic and Gamma_Data accompanying the unique gamma ray in FIGS. 6a and 6b correspond to those that are not from the unique gamma ray detector 20, but from the PET detectors 10.

By executing the hardware processing in the imaging processor as mentioned above, sorting of signals or data for Combinations I and II of probes can be performed in the logic unit 342 in the dedicated and dual-use operations respectively.

Sorting at the logic unit 342 is carried out in Combination I with a plurality of Type-B probes regarding data for pair annihilations with a unique gamma ray by the energy of the unique gamma ray. In Combination II using Type-A and Type-B probes, pair-annihilation gamma rays are sorted into ones without a unique gamma ray, and ones with a unique gamma ray. The more detailed implementation will be described later in Embodiments 1 and 2 respectively for Combinations I and II later.

It should be noted that contrasting descriptions for the dedicated and dual-use operations are made as typical implementations provided only for the purpose of clear description of the operation at the logic unit 342 in the image processor 30 in FIG. 4. In addition, the description should not be considered to exclude additional operations that are not specifically described. For example, it is possible to reduce amount of data to be processed considerably, if upper and lower limits of the energy values are set as a hardware implementation in a hardware processing circuitry (not shown), or practicing "energy gating," and logic signal such as the signal Gamma_Logic is output to the hardware processing circuit only when the energy falls within the limitations.

3. Nuclides

In the present embodiment, nuclides that emit a unique gamma ray following the positron emission by the beta decay, or Type-B nuclides, are used for labelling the Type-B probe mentioned above. The Type-B nuclides can be selected with various viewpoints. Even though a nuclide, or a parent nuclide, first makes transition with emitting positron through beta decay to an excited state of its daughter nuclide, and then the daughter nuclide makes transition by gamma decay with emission of a unique gamma ray to a ground state, such a nuclide or the nuclear isomer may be inappropriate for the coincidence measurement if it takes too long from the positron emission to the unique gamma ray emission. The period of time from beta decay to gamma decay, or lifetime of the excited state of the daughter nuclide, ranges from the order of femtoseconds for shorter ones to the order of months or more for longer ones. The criterion for the lifetime in adopting Type-B nuclide in the present embodiment may be determined in comparison with temporal response of the detectors. That is, for suppressing fraction of accidental coincidence measurement thereby improving the signal-to-noise ratio, it is favorable to make the lifetime of the excited state of the daughter nuclide to be comparable to, or shorter than the temporal resolution of used gamma ray detectors.

Still a large number of nuclides meet this criterion for a Type-B nuclide. Table 3 lists promising nuclides among others.

TABLE 3

USEFUL NUCLIDES FOR PET DEVICE FOR SIMULTANEOUS IMAGING ON MULTI-TRACER

| Nuclide | Half-Life | | $e^+$ emission rate (%) | $\gamma$ ray energy (keV) (emission rate (%)) | Production (Typ.) |
|---|---|---|---|---|---|
| $^{14}$O | 70.6 | sec | 99.9 | 2312.5 (99.4) | Small scale cyclotron |
| $^{38}$K | 7.6 | min | 49.9 | 2167.5 (99.9) | Cyclotron, etc. |
| $^{44}$Sc | 3.927 | hr | 94.3 | 1157 (94.1) | Small scale cyclotron |
| $^{48}$V | 16.0 | day | 49.9 | 983.5 (99.98) | Small scale cyclotron |
|  |  |  |  | 1312.1 (98.2) |  |
| $^{52m}$Mn | 21.1 | min | 95 | 1434.1 (98.3) | $^{52}$Fe generator |
| $^{60}$Cu | 23.7 | min | 92.5 | 826.4 (21.7) | Small scale cyclotron |
|  |  |  |  | 1332.5 (88.0) |  |
|  |  |  |  | 1791.6 (45.4) |  |
| $^{76}$Br | 16.2 | hr | 54.5 | 559.1 (74.0) | Small scale cyclotron |
|  |  |  |  | 657.0 (15.9) |  |
|  |  |  |  | 1853.7 (14.7) |  |
| $^{82}$Rb | 1.3 | min | 95.5 | 776.5 (15.1) | $^{82}$Sr generator |
| $^{94m}$Tc | 52.0 | min | 70.2 | 871.1 (94.2) | Small scale cyclotron |
| $^{124}$I | 4.2 | day | 22.5 | 602.7 (62.9) | Small scale cyclotron |
|  |  |  |  | 722.8 (10.4) |  |
|  |  |  |  | 1691.0 (11.2) |  |
| $^{22}$Na | 2.6 | year | 90.4 | 1274.5 (99.9) | Small scale cyclotron |

Note that the property data values for nuclides in Table 3 were chosen and extracted by the inventors for the illustration purposes from a treatise "Table of Isotopes" by R. B. Firestone, 8th Edition, John Wiley and Sons (1998), and from "decay radiation" data for individual specified nuclide on a website, http://www.nndc.bnl.gov/chart/, served by National Nuclear data Center, Brookhaven National Laboratory. The values in column "half-life" in Table 3 are ones for beta decay corresponding respective parent nuclides indicated in column "nuclide." Thus these values are not ones of gamma decay from excited state of its daughter nuclides.

We list factors to be considered in selection of useful nuclides in practicing the present embodiment, as follows: "half-life of beta decay", "emission probabilities of a positron and a unique gamma ray", "energy of the unique gamma ray", "(maximum) energy of the positron", "availability in nuclide supply", and "easiness in labeling agents."

The "half-life of beta decay" relates to lifetime of the beta decay from the parent to daughter nuclide. If the half-life of beta decay is too short, conducting labeling agent, administering the agent to the subject to be imaged, and image capturing will be difficult. On the other hand, if the half-life of the beta decay is too long, internal exposure lasts too long to be applied for clinical use. Considering these, appropriate half-life of the beta decay in the present embodiment for the clinical application should be from the order of minutes to the order of days. In fact, half-lives of beta decay for nuclides frequently used in the conventional PET device are 20.4 min ($^{11}C$) and 109.8 min ($^{18}F$). Moreover, especially for the clinical applications, if a daughter nuclide is radioactive isotope with long lifetime after the beta decay, it will cause long period of internal exposure; however, the daughter nuclides listed in Table 3 are all stable isotopes.

The "positron emission probability" is a ratio for a positron to be emitted per decay, and the "unique gamma ray emission probability" is a ratio for a unique gamma ray to be emitted for each positron emission. It is generally preferable if both of the emission probabilities of positron and unique gamma ray have grater values; however the ranges are not specifically limited. This is because seemingly low positron emission probability nuclide, such as $^{64}Cu$, with the probability of 17.6%, may also be used in an imaging demonstration in current PET. Among other things, when it comes to Type-B nuclide, it is preferable to use a nuclide with high probability of the unique gamma ray after positron emission. It is to be noted that listed ones in the unique gamma rays in Table 3 have the emission probability after the positron emission of 10% or more.

As for the "energy of the unique gamma ray," in the first place, the energy of the unique gamma ray should be different from 511 keV, which is gamma ray energy for positron pair-annihilation. Moreover in the present embodiment, it is advantageous to use energy of unique gamma ray greater than 511 keV. This is because broader energy window of full energy range higher than 511 keV may be adopted for a unique gamma ray. However, it may be difficult to detect extremely high energy gamma ray. Also, when a unique gamma ray has energy of 1022 keV or more, it may lead to creation of positron due to electron pair production and such a positron may further make pair annihilation to produce 511 keV gamma rays, which would generate noise in PET imaging.

The "(maximum) energy of the positron" is energy of positron emitted through the beta decay. The smaller the energy is, the shorter the average range of travel of positrons before the pair annihilation occurs, which may reduce the positional shift between the position of the pair annihilation and the position of the positron emitting nucleus. This means that, in terms only of the resolution in the general PET device including the present embodiment, small values for the (maximum) energy values of the positron would be preferable. However, high energy nuclide may be adopted depending on the accuracy required.

The "availability in nuclide production and supply" is, in short, smallness of the scale of producing device of nuclides, or related costs. The production and supply thereof should be easy for the purpose of wide use of nuclides. In particular, medical institutions where PET devices are installed usually have small scale cyclotron onsite to produce positron emitting nuclides these days. Therefore, it is preferable that Type-B nuclides can be produced with relatively low energy nucleus transmutation by the small scale cyclotron. Since several kinds of nuclides are produced concurrently when a Type-B nuclide is produced due to nucleus transmutation by the cyclotron, it is also preferable if the nuclide of interest is easily isolated. Furthermore, a nuclide produced as a daughter nuclide trough beta decay from its parent nuclide having relatively longer half-life, or milking, is also preferable, because such a parent nuclide can be distributed to various sites after production at one facility. The indications of production with "small cyclotron" in Table 3 denote that corresponding nuclides can be produced by charge exchange reaction, for example $^{14}N(p,n)^{14}O$ reaction for producing $^{14}O$, by positron beam with energy of 20 MeV or less, which is assumed for medical cyclotrons. A nuclide that requires beam of 20 MeV or more is indicated with "cyclotron, etc."

The "easiness in labeling agents" is related to a viewpoint as to whether nuclide is easily utilized for labeling organic compound agents or not. For example, even an element prone to form a compound, such as halogen, or metal, such an element may be often used easily for labeling agent if the element can form a complex (metal compound). It is to be noted that rare gas elements that are hard to form compound may be used as a probe in a form of the simple substance of the element.

It should be noted that the factors for the selection criteria may be adjusted regarding which factors or how much degree should be considered, depending on how the PET device of the present embodiment is used. For example, $^{22}Na$ listed in the Table 3 is not suitable for clinical application due to its long half-life; it is useful for animal studies or experiments conducted with phantoms, because it has been widely used as a standard radiation source.

In the fundamental schemes of the present invention described above, simultaneous imaging on multi-tracers can be practiced while taking advantages of superior quantitative performance of the PET device.

<Embodiment 1>

4. Embodiment for Administering Plural Type-B Probes

In what follows, as Embodiment 1 of the present invention, further detailed scheme for capturing images for a plurality of probes by the PET device having fundamental structures described in Fundamental Embodiment will be described. The Embodiment 1 describes an embodiment adopting Combination I in which a plurality of Type-B probes are used, as described in the Fundamental Embodiment.

4-1. Operation

Figure 7:
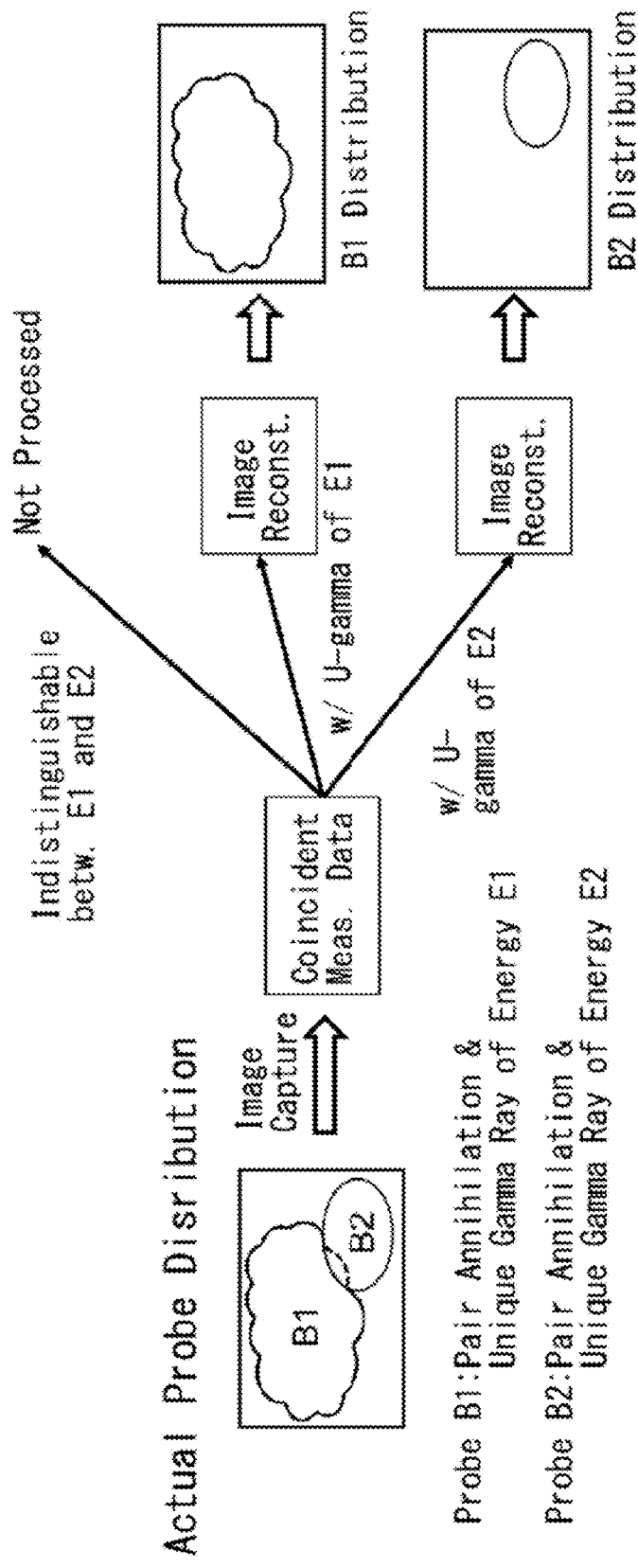
FIG. 7 is an explanatory chart indicating general processing operation in an embodiment in the present invention, in which a plurality of Type-B probes are administered.

FIG. 7 is an explanatory chart indicating general processing operation in the present embodiment, in which a plurality of Type-B probes is administered. In the present embodiment, plurality types of the Type-B probes that are distinct with each other are simultaneously administered to a subject to be imaged, and respective distributions of probes are to be identified. Respective probes are called Probes B1 and B2, and respective nuclides used for the probes are called Nuclides B1 and B2. The Probes B1 and B2 are assumed to emit unique gamma rays with energy values E1 and E2 respectively, following respective pair annihilations. Thus, measurement data obtained at the imaging processor 30 is used to reconstruct distribution images, the distribution image of Probe B1 from data associated with the energy E1, whereas the distribution image of Probe B2 from data associated with the energy E2. Data that is not associated either of the energy values will not be used in image reconstruction (FIG. 7).

In the Embodiment 1, the imaging processor 30 (FIGS. 3 and 6a) determines the energy values of the unique gamma ray to be energy E1, E2, or something else for executing operation indicated in FIG. 7. Therefore, the sorting processing in the present embodiment in which a plurality of Type-B probes are administered is to make determination based on energy of the unique gamma ray at the imaging processor 30, or more specifically, the logic unit 342.

4-2. Probes

In a typical example, Probes B1 and B2 are selected as agents that would accumulate in respective living areas where mutually different biological functions develop, i.e., that is, agents that would accumulate in different tissues within living body or the like, according to different mechanisms, and are distinctive with each other. Nuclides B1 and B2 used to label Probes B1 and B2 respectively are selected as a combination that allows distinction of energy values E1 and E2 of respective unique gamma rays from each other, among such nuclides as listed ones in Table. 3.

<Embodiment 2>

5. Embodiment for Administering Type-A and Type-B Probes

In what follows, further detailed scheme will be described as Embodiment 2 of the present invention, in which Combination II with Type-A and Type-B probes for capturing images are adopted for a plurality of probes, as described in the Fundamental Embodiment. Also in this embodiment, imaging will be conducted by a PET device for simultaneous imaging on multi-tracers having fundamental structure as described in the Fundamental Embodiment.

The present embodiment is also practiced in two structures, one that does not use energy of gamma rays in the measurement and the other that uses such energy. In the following description, a structure and probes common to both of them will be described first (5-1 and 5-2), and then the structures will be described respectively (5-3 and 5-4).

5-1. Operation

Figure 8:
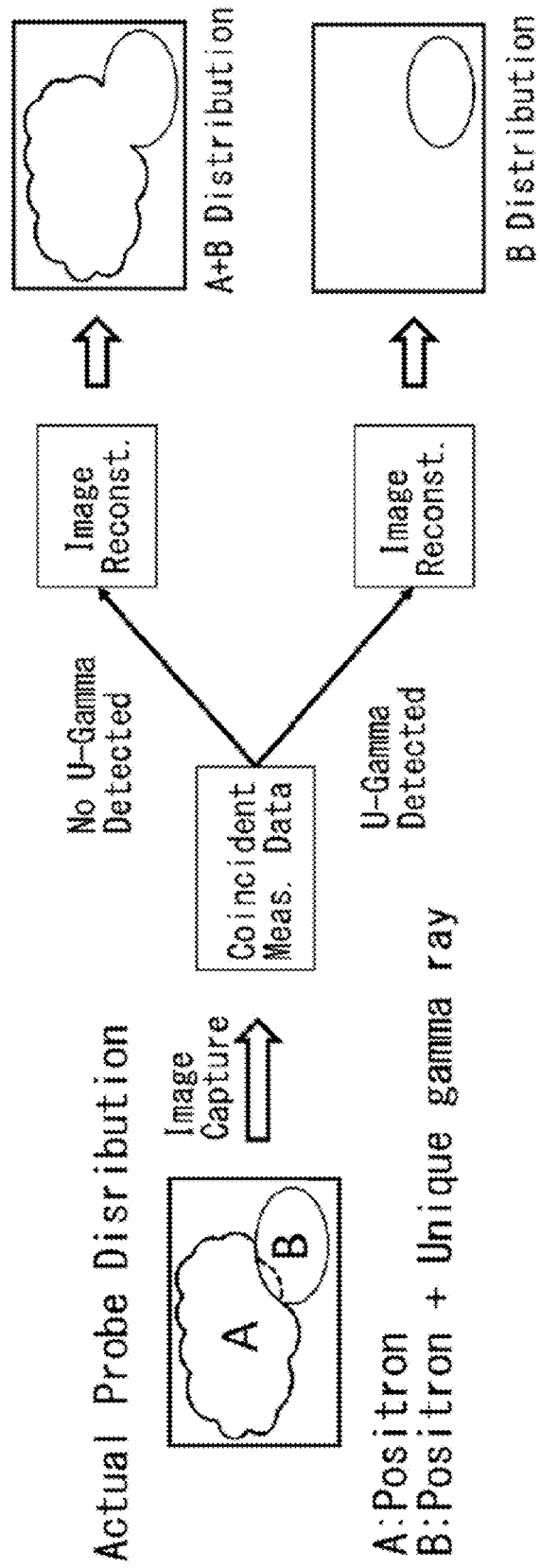
FIG. 8 is an explanatory chart indicating general processing operation in an embodiment in the present invention, in which Type-A and Type-B probes are administered.

FIG. 8 is an explanatory chart indicating general processing operation for the present embodiment, in which Type-A and Type-B probes are administered. In the present embodiment, a type of probe that has been used in the conventional PET device, or a Type-A probe, and another type of probe that emits unique gamma ray, or a Type-B probe, are administered simultaneously to a subject to be imaged and the probes are identified.

That is, a pair of gamma rays of 511 keV, or pair-annihilation gamma rays, reflects both distributions of Type-A and Type-B probes. Among all events for detections of the pair-annihilation gamma rays, events measured coincidentally with unique gamma rays are associated with Type-B probe distribution. In contrast, among all the events mentioned above, events that are determined as not measured coincidentally with the unique gamma rays reflect not only Type-A probe distribution, but Type-B distribution as well. This is because not all of the unique gamma rays emitted by the Type-B probe are detected.

Therefore, in the measured data obtained in the imaging processor 30, what are to be reconstructed are, a Type-B probe distribution image from data associated with the unique gamma rays, and a superimposed image of images for a Type-A probe distribution and a Type-B probe distribution from data not associated with the unique gamma rays (FIG. 8).

For the operation indicated in FIG. 8 to be carried out in Embodiment 2, the imaging processor 30 determines as to whether a unique gamma ray as an indicative of Type-B probe has been coincidentally detected or not at the timing of the coincidence measurement of the pair-annihilation gamma rays. Thus, sorting by whether a unique gamma ray has been detected or not in the imaging processor 30, in particular at the logic unit 342, corresponds to a typical sorting processing (FIGS. 3 and 6*b*). Also in the imaging processor 30 (the logic unit 342), it is possible to obtain measured energy of the unique gamma ray from the signals PET1_Data and PET2_Data and the signal Gamma_Data, for carrying out sorting of the Type-A and Type-B probes by the value of the energy. A case when measured energy of the unique gamma ray is not used and a case when it is used will be described later (in sections 5-2 and 5-3, respectively).

5-2. Probes

A probe for the conventional PET device is adopted for a Type-A probe in the present embodiment, whereas a probe labeled by a nuclide that emits unique gamma ray following the positron emission is adopted for a Type-B probe. As has been described in Fundamental Embodiment, various kinds of nuclides can be adopted for the Type-B probe. Typically, any nuclides exemplified in Table 3 may be adopted. The energy of the unique gamma ray in this regard may be arbitrary as long as it can be distinguished from 511 keV. For example, if a nuclide with energy of more than 511 keV is selected, such a nuclide is advantageous for wider energy window setting, in which any energy value in a range above 511 keV can be attributable to that of unique gamma rays.

5-3. When Energy of Unique Gamma Ray is Not Used

It is not always necessary to use an energy value of unique gamma ray in practicing operation indicated in FIG. 8. Note that it is possible that the energy resolution capability is not used even when the unique gamma ray detector 20, or energy-resolving gamma ray detector, is adopted for this operation. When triple fold coincidence measurement among pair-annihilation gamma rays and a unique gamma ray is conducted without using the energy, noise may accompany images, because of nature of Type-B probe, from which three pencils of gamma rays are created and emitted as the pair-annihilation gamma rays and a unique gamma ray, or because of the detector arrangement. The noise generation and a countermeasure thereto will be described.

5-3-1. Mechanism of Noise

Figure 9:
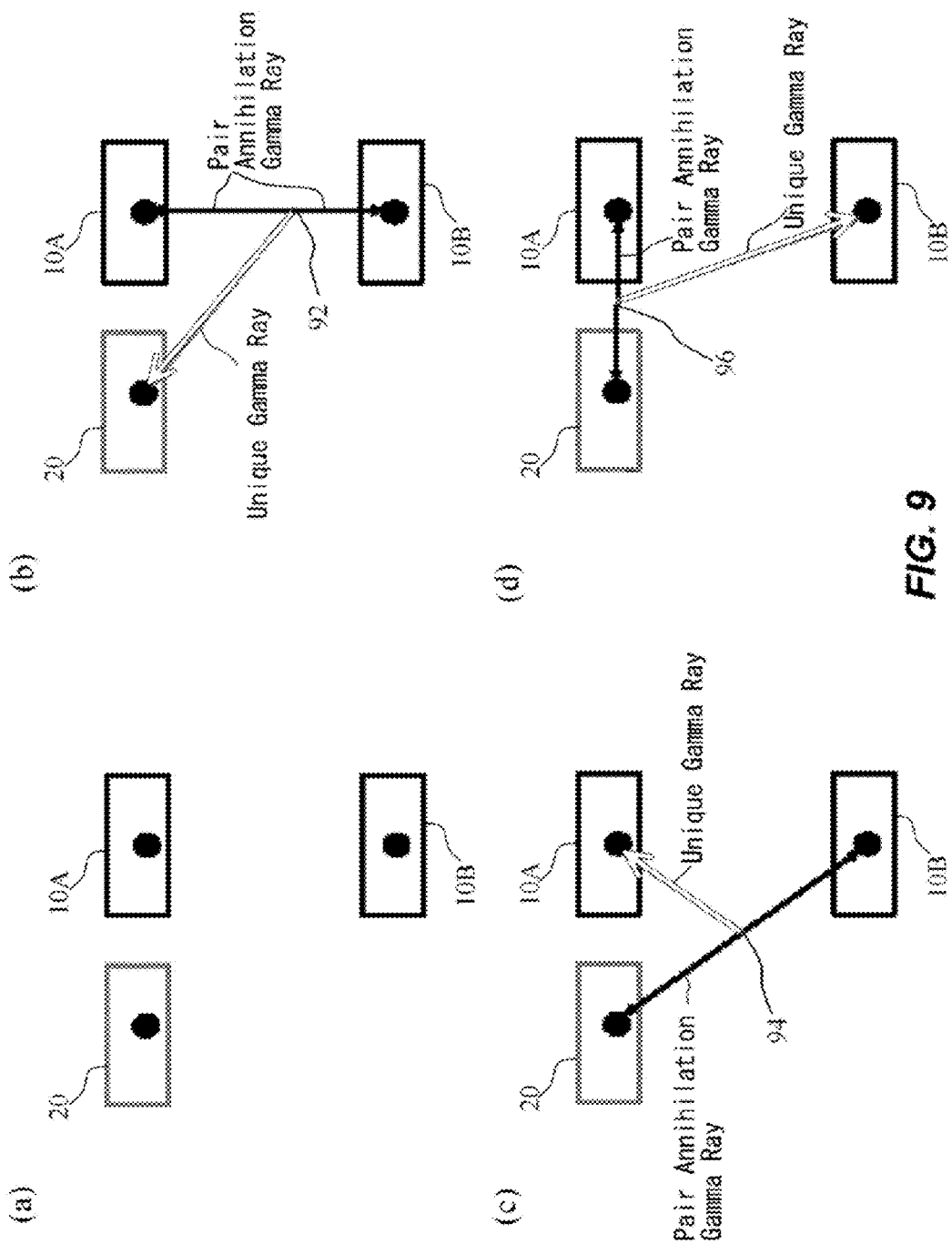
FIG. 9 is an explanatory diagram indicating generation mechanism of noise in an embodiment in the present invention, in which Type-A and Type-B probes are administered, but energy detection of unique gamma rays is not used for the image capturing.

FIG. 9 is an explanatory diagram indicating generation mechanism of noise, in which Type-A and Type-B probes, or probes for Combination II, are administered, but an energy value of unique gamma rays is not used for image capturing. More specifically, FIG. 9*a* depicts an arrangement of the detectors, with a cross sectional view cut with a plane along an axis of a ring of the PET detectors 10, which are arranged in the ring shape as indicated in FIG. 3. The solid circles indicated on the detectors denote positions where gamma rays have been detected in the detectors. FIGS. 9*b*-9*d* illustrate combinations of respective gamma rays and interactions at detectors for: a case when an event effective for image reconstruction was detected, or proper detection took place (FIG. 9*b*), and cases when an event not effective for image reconstruction was detected, or improper detection took place (FIGS. 9*c* and 9*d*). In FIG. 9, PET detectors 10 and a unique gamma ray detector 20 are indicated only those that are related to the description. Moreover, for distinguishing each detector in the PET detectors 10, depicted ones in the drawing in the upper and lower portions will be referred as PET detectors 10A and 10B respectively.

Let's assume gamma rays were detected in the detectors arrangement in FIG. 9*a* and a triple coincidence measurement was conducted. In this regard, it is highly probable that two pencils of the pair-annihilation gamma rays and a pencil of unique gamma ray have been actually detected. However, the combinations of the detectors and gamma rays for which the triple coincidence measurement has been conducted include following three cases. One is a case when the unique gamma ray entered into the unique gamma ray detector 20, as it had been expected. In such a case, the pair-annihilation gamma rays have interacted with PET detectors 10A and 10B respectively and the unique gamma ray has interacted with the unique gamma ray detector 20. On the other hand, in cases when the PET detector 10A has detected the unique gamma ray (FIG. 9c) and when the PET detector 10B has detected the unique gamma ray (FIG. 9d), such detections are not as expected ones.

If energy values of gamma rays are not used, the respective detectors cannot distinguish the unique gamma ray from the pair-annihilation gamma rays; thus, it is difficult to determine which combination of FIGS. 9b-9d occurred in the actual detection only by determining the triple fold coincidence measurement. For such a situation, only detection timing of gamma rays in the output of the unique gamma ray detector 20, or energy-resolving gamma ray detector, is used. As a result, the subsequent processing will be carried out even for cases of FIGS. 9d and 9d, as if the events were the case of FIG. 9a. The signals to be used in the image creation, or signals from two PET detectors 10A and 10B, include a mixture of a signal based on a proper event indicated in FIG. 9a and signals based on improper events indicated as in FIGS. 9b and 9c. Eventually the signals based on improper events in FIGS. 9b and 9c will generate noise.

Since there is no correlation on angles among radiation directions of the unique gamma ray and the pair-annihilation gamma rays, the noise mentioned above is generated randomly. That is, in cases when the unique gamma ray enters PET detector (FIG. 9c or 9d), position estimates by straight lines connecting PET detectors 10A and 10B yield positions that have no relationship with position where the gamma ray has actually emitted. Therefore, degradation on image quality given by statistical fluctuation by such random noise may become less significant for image capturing in which sufficient amount of statistical samples are obtained. The statistical fluctuation in this respect, however, will degrade image quality for imaging with insufficient statistical samples. In such case, it is preferable to reduce noise by one or both of suppressing noise by way of detectors arrangement (described below in 5-3-2), and discriminating unique gamma ray with energy values (described below in 5-4).

5-3-2. Detectors Arrangement for Noise Suppression

Figure 10:
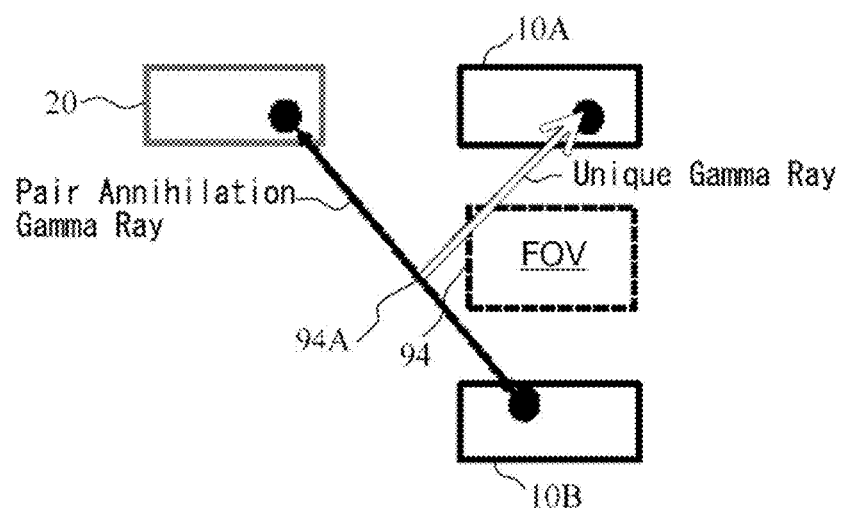
FIG. 10 is an explanatory diagram of an example arrangement of detectors for suppressing noise in an embodiment in the present invention, in which Type-A and Type-B probes are administered, but energy detection of unique gamma rays is not used for the imaging.
Figure 10:
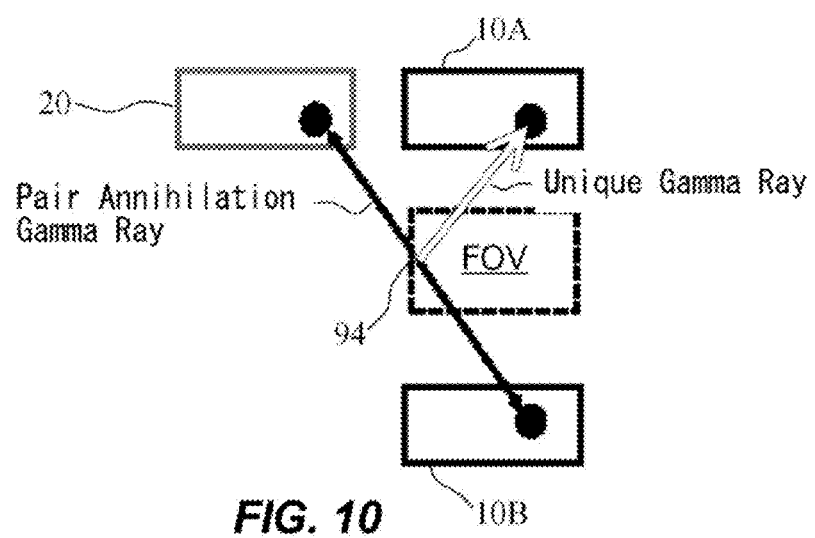

It is possible to reduce the noise by adjusting arrangement of unique gamma ray detector 20 even when the gamma ray energy is not detected. FIG. 10 is an explanatory diagram of an example arrangement of detectors for suppressing noise, in a combination where Type-A and Type-B probes are administered, but energy detection of unique gamma rays is not used for the imaging. FIG. 10a indicates an arrangement example in which the arrangement of the PET detector 10 and the unique gamma ray detector 20 is changed to reduce the noise, whereas FIG. 10b indicates a case without such change and the noise may be generated. The FOV denotes a spatial area that is defined as an area where the image can be captured in the PET device.

Here we assume that the probe distributes over the interior of the FOV only, which is defined by arrangement of the PET detectors 10. Even when beta decay takes place within the FOV, the combination of detectors that has detected gamma rays may be, as indicated in FIG. 10b, such that the unique gamma ray detector 20 and PET detector 10B have detected the pair-annihilation gamma rays, and the PET detector 10A has detected the unique gamma ray. If the events in FIG. 10b are used for image reconstruction, image noise will be generated, because the proper positions of creation of the pair-annihilation gamma rays are not obtained. In contrast, by changing the arrangement of unique gamma ray detector 20 as in FIG. 10a, it is possible to suppress the influence of the noise. That is, by changing the arrangement such that a straight line connecting unique gamma ray detector and PET detector does not pass the FOV, two pencils of pair-annihilation gamma rays oppositely emitted to make 180 degree angle do not enter into the unique gamma ray detector.

The arrangement may be defined by a group of imaginary straight lines connecting each point in the unique gamma ray detectors 20 and each point in the PET detectors 10. The change of the arrangement of the unique gamma ray detector 20 for suppressing noise in FIG. 10a is equivalent to reducing the number of straight lines that pass the FOV as much as possible in the above-mentioned group of the straight lines. It is most preferable that no single straight line passing the FOV is included in the above-mentioned group of straight lines. That is, in the arrangement change mentioned above, it is possible to adopt only a combination of unique gamma ray detector and the PET detectors arranged in such a manner that straight lines there never pass the FOV, for image capturing for Type-B probe. By changing the arrangement of the unique gamma ray detector 20 as mentioned above, it is possible to effectively suppress noise caused by entry of unique gamma ray to the PET detectors.

It should be noted that actual probe distribution is not limited to inside of the FOV. If the probe distributes over outside FOV too, the use of shield as stated in section 2-3 in addition to the arrangement change mentioned above may reduce the noise. This is because shielding gamma ray entering from outside of FOV into the unique gamma ray detector excludes improper events as in FIGS. 9b and 9c, which leads to suppression of noise.

5-4. Use of Energy Value of Unique Gamma Ray

The proper detection of events indicted in FIG. 9b, and events that would generate noise as indicated in FIGS. 9c and 9d may be distinguished by use of energy value detected at the unique gamma ray detector 20. That is, determination is made as to whether the gamma rays detected in the unique gamma ray detector 20 has the energy value for the unique gamma ray of Type-B probe, or one for the pair-annihilation gamma rays. Once the gamma ray detected by the unique gamma ray detector is determined as a unique gamma ray, it follows that the gamma rays detected at the PET detectors are concluded as pair-annihilation gamma rays; thus events to be used in the image reconstruction can be limited to proper ones. Accordingly, only proper events can be used for the image reconstruction, and the noise mentioned above can be suppressed.

It should be noted that, when discrimination between pair-annihilation gamma rays and unique gamma rays is incomplete due to limitations of the energy resolution of the detector or the like, the noise suppression by the detector arrangement change mentioned above and discrimination based on the energy value may be combined, which leads to improved accuracy of extraction of events that is effective for image reconstruction.

<Demonstration Example>

To validate the effectiveness of embodiments mentioned above, simulation of numerical calculation by Mote Carlo method has been conducted as a demonstration example of Embodiment 2.

6. Validation Example by Simulation

Monte Carlo method was adopted for the simulation. We used "Geant 4", a generic tool for simulating interactions between radiation and substance, as a program code for the simulation. Geant 4 is available at http://www.geant4.org/geant4/.

6-1. Condition for Simulation

The conditions of setting reproduced on a computer for the simulation of numerical calculation were as follows.

(PET Detectors 10 (FIG. 3))
    PET detectors arrangement (outline): Arrangement mimicking a PET Device for small animals (Focus 220, Siemens, Germany)
    Type of PET detectors: LSO scintillator, 4 mm×4 mm, thickness 10 mm
    624 in ring circumferential direction x 52 in ring width direction,
    260 mm for ring inner diameter, 76 mm for ring width,
(Unique Gamma Ray Detector 20 (FIG. 3))
    Germanium semiconductor detector, 40 mm×40 mm, 20 mm thickness
    32 detectors (2 rings of 16 detectors), 250 mm for ring inner diameter
(Phantom Shape (FIG. 11))
    Type-A and Type-B nuclides, distributed uniformly over the interior of respective spheres of 20 mm radius
    Overlap of the spheres: 20 mm
    Type-A nuclide: $^{18}$F
    Type-B nuclide: $^{94m}$Tc (gamma ray emission rate: 94.2%, energy: 871.1 keV)
    Total number of events: $4 \times 10^9$ ($2 \times 10^9$ events respectively for Type-A and Type-B)
    Operation scheme: dedicated operation
(Image Reconstruction Method)
    3 dimensional OSEM (ordered subset estimation maximization maximum likelihood method)

Figure 11:
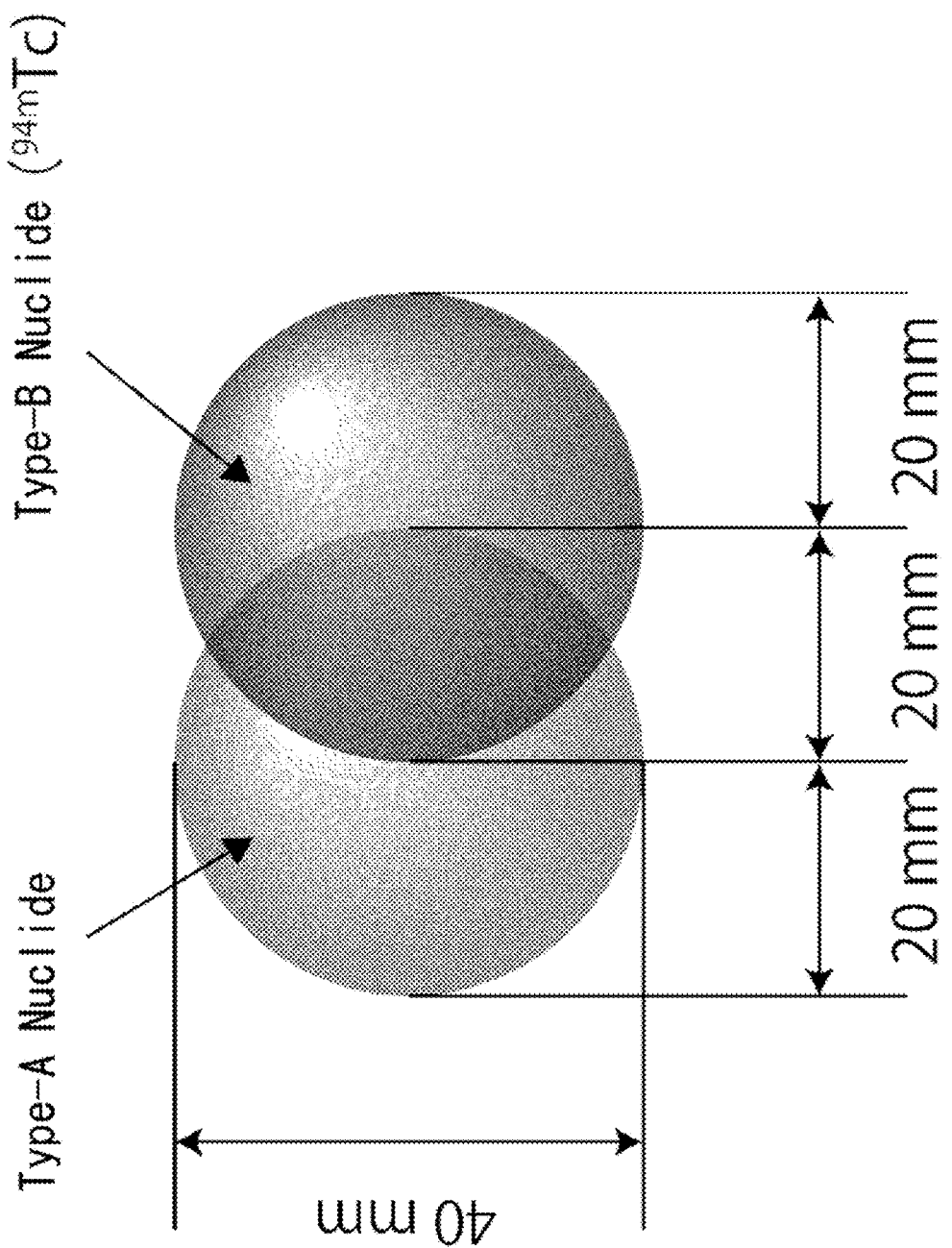
FIG. 11 is a schematic diagram illustrating shapes of phantoms that give probe distributions for which numerical simulation is conducted in an embodiment in the present invention.

A phantom is, generally speaking, an object used for calibration in place of the subject to be imaged such as living body, and artificial object that can be configured to have known shape and known radioactivity. However, in the numerical simulation, a virtual spatial distribution of probe established inside of a computer is also called a phantom. FIG. 11 is a diagram illustrating shapes of phantoms that give probe distributions for the subject to be imaged with which the present numerical simulation is conducted.

Furthermore, the number of events used for the simulation, as indicated above, is the number of repetition defined by the number of positron emission from a probe, and corresponds to image capturing of 2 MBq each for Type-A and Type-B for 1000 seconds. The positron emission rate was set to 100%. Moreover, dead time in the hardware and decay of radioactivity were not taken into account. Since the operation has been assumed to be the dedicated operation, unique gamma ray detection by the PET detectors has never been reflected in the calculation. On top of that, a condition was adopted in which gamma rays with energy in entire range of 520 keV or higher detected at the unique gamma ray detectors were deemed to be unique gamma ray, as a discrimination condition with energy of unique gamma ray from the pair-annihilation gamma ray.

6-2. Simulation Results

The Monte Carlo simulation with the conditions indicated above revealed that counting rate per one unique gamma ray detector was $6.6 \times 10^4$ count/second (including all events of all energy) for 4 MBq for Type-A and Type-B altogether. Such a counting rate can be easily handled without any difficulty if a fast signal processing device is adopted. Moreover, the detection rate of unique gamma rays in the total number of detections of pair-annihilation gamma rays, including both Type-A and Type-B nuclides by the PET detector, was 3.9%. This calculation result reflects emission probability of the unique gamma ray.

Figure 12:
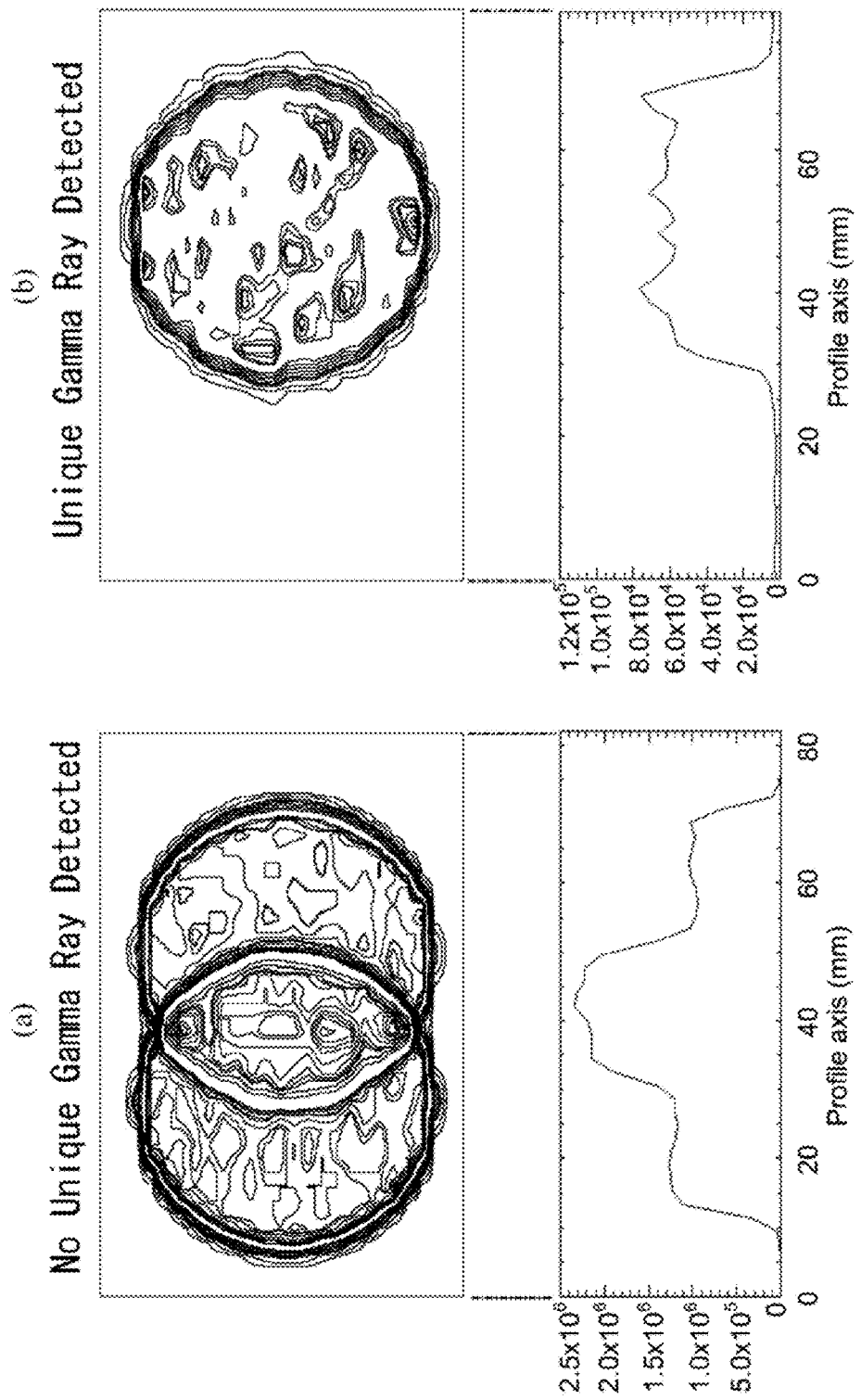
FIG. 12 is an image captured for phantoms obtained by the numerical simulation in an embodiment in the present invention.

A three dimensional image with 0.8 mm voxel size was reconstructed for the simulated data of the phantom mentioned above for the subject to be imaged. FIG. 12 indicates a profile on a cross sectional plane that passes both centers of the spheres, inside of which Type-A and Type-B probes have been distributed, and oriented perpendicular to an axis of symmetry of the group of PET detectors. FIG. 12a indicates two and one dimensional radioactivity profiles of an image reconstructed only for pair annihilation events with which no unique gamma ray has been detected at the unique gamma ray detector 20 through the present simulation. As indicated in the top portion in FIG. 12a, the image of pair annihilation events without detection of a unique gamma ray has been reconstructed as a superimposed image having a distribution image of Type-A probe of a circular disc corresponding to a cross section of a sphere, and another distribution image of Type-B of a similar circular disc, superimposed with each other while being shifted their centers, as though they reflect the arrangement of the phantom. One dimensional radioactivity profile in the bottom portion in FIG. 12a indicates radioactivity in the vertical axis over a straight line passing the centers of the both probe distributions. The one dimensional profile in FIG. 12a shows that uniform intensities of radioactivity for each probe have been observed, except the fluctuation mentioned above. Also the one dimensional profile in FIG. 12a shows that total values of radioactivity for each probe has been observed in the overlapping portion of the probes.

Furthermore, FIG. 12b indicates two dimensional and one dimensional radioactivity profiles of an image reconstructed for pair annihilation events accompanied by unique gamma ray detection at the unique gamma ray detector 20 through the present simulation. As indicated in the top portion in FIG. 12b, the two dimensional profile for pair annihilation events with detection of a unique gamma ray included only distribution image of Type-B probe, without influenced by the Type-A probe at all. One dimensional radioactivity profile in the bottom portion in FIG. 12b shows that uniform intensities of radioactivity for Type-B probe have been observed, except the fluctuation mentioned above, and that no influence by the Type-A probe was found.

Although FIG. 12 indicates that statistical fluctuation is inescapable for the image estimation through the finite number of events in Embodiment 2, it has been confirmed that images of Type-A and Type-B probes were reconstructed separately.

The reason why the Type-B probe distribution is reflected in an image of pair annihilations without unique gamma ray detection in FIG. 12a is that, despite the fact that the unique gamma ray was emitted with a probability of 94.2%, events whose unique gamma ray has never been caught by the unique gamma ray detector 20, or events of "missed" detection, are also used in the reconstruction together with pair-annihilation gamma rays by the Type-A probe. The missed detection of the unique gamma ray may be mitigated by, such as, increasing a total of solid angles that are subtended by a group of unique gamma ray detectors 20 against the subject to be imaged. However, increasing the number of unique gamma ray detectors 20 to have greater total solid angle may lead to interference to the subject to be imaged or to PET detectors 10. Thus, for determining arrangement of the group of unique gamma ray detectors 20 or their sizes, various conditions related to practical aspect will be considered.

The embodiment of the present invention has been described specifically throughout the above description. Any description in this Specification is for the purpose of explaining the present invention; therefore the scope of the invention should be determined based on recitations of the claims. Furthermore, other variation based on any combination of the embodiment is included in the present invention, which variation should be also within a scope of the present invention.

INDUSTRIAL APPLICABILITY

According to the present invention, imaging with differentiating a plurality of probes with each other is realized. Accordingly, the present invention enables simultaneous imaging on multi-tracers and contributes to spreading diagnostic devices for nuclear medicine or research instrument of tracer imaging.

REFERENCE SIGNS LISTS

100 PET device for simultaneous imaging on multi-tracer
10 PET detector (PET gamma ray detectors, energy resolving gamma ray detector)
20 unique gamma ray detector (energy-resolving gamma ray detector)
22, 24 outer surface
30 imaging processor
32 coincidence determination unit
322 logic unit
324 gate unit
34 data sorting unit
342 logic unit
36 image reconstructing unit
362, 364 image reconstructing processor
612, 614, 622, 624 AND
616, 626, 628 Gate

What is claimed is:

1. A positron emission tomography (PET) device for imaging a plurality of probes comprising:
   a group of PET gamma ray detectors adapted to receive a pair of pair-annihilation gamma rays from a subject to be imaged, wherein the pair of pair-annihilation gamma rays are generated by a positron-electron pair annihilation, and wherein to the subject to be imaged both of a first probe and a second probe are administered, the first probe having a positron emitting nuclide that becomes an excited state of a daughter nuclide through beta decay and, following a positron emission by the beta decay emits a unique gamma ray of a first energy during transition into a ground state of the daughter nuclide, and the second probe having a nuclide that becomes an excited state of a daughter nuclide through beta decay and, following a positron emission by the beta decay, emits a unique gamma ray of a second energy during transition into a ground state of the daughter nuclide,
   an energy-resolving gamma ray detector adapted to detect one of the unique gamma rays for resolving the first energy and the second energy; and
   an imaging processor that receives both of a pair-annihilation detection signal supplied according to coincidence measurement with a pair of PET gamma ray detectors in the group of PET gamma ray detectors and a signal supplied by the energy-resolving gamma ray detector, wherein the imaging processor executes reconstruction of images for the pair-annihilation detection signal differently according to whether an energy value of a unique gamma ray detected within a predetermined time of the detection of the pair-annihilation gamma rays corresponds to the first energy or the second energy.

2. The PET device according to claim 1, wherein a gamma ray detector that works as the energy-resolving gamma ray detector is a gamma ray detector provided separately from the group of the PET gamma ray detectors.

3. The PET device according to claim 1, wherein a gamma ray detector that works as the energy-resolving gamma ray detector is at least one gamma ray detector in the group of the PET gamma ray detectors.

4. The PET device according to claim 1, wherein the group of PET gamma ray detectors is a group of scintillation detectors.

5. The PET device according to claim 1, wherein the group of PET gamma ray detectors is a group of semiconductor gamma ray detectors.

6. The PET device according to claim 1, wherein the energy-resolving gamma ray detector is a scintillation detector.

7. The PET device according to claim 1, wherein the energy-resolving gamma ray detector is a semiconductor gamma ray detector.

8. The PET device according to claim 1, wherein the energy-resolving gamma ray detector is provided with a shield for shielding gamma rays coming from outside of filed-of-view for the group of PET detectors.

9. The PET device according to claim 1, wherein the energy-resolving gamma ray detector is arranged in such a way that any straight line connecting each energy-resolving gamma ray detector and each PET detector does not pass through field-of-view for the group of PET detectors.

10. A positron emission tomography (PET) device for imaging a plurality of probes comprising:
    a group of PET gamma ray detectors adapted to receive a pair of pair-annihilation gamma rays from a subject to be imaged, wherein the pair of pair-annihilation gamma rays are generated by a positron-electron pair annihilation, and wherein to the subject to be imaged both of a first probe and a PET probe are administered, the first probe having a nuclide that becomes an excited state of a daughter nuclide through beta decay and, following a positron emission by the beta decay emits a unique gamma ray during transition into a ground state of the daughter nuclide, and the PET probe having a positron emitting nuclide that mainly becomes a ground state of a daughter nuclide through beta decay,
    an energy-resolving gamma ray detector adapted to receive the unique gamma ray emitted by the first probe; and
    an imaging processor that receives both of a pair-annihilation detection signal supplied according to coincidence measurement with a pair of PET gamma ray detectors in the group of PET gamma ray detectors and a signal supplied by the energy-resolving gamma ray detector, wherein the imaging processor executes reconstruction of images for the pair-annihilation detection signal differently according to whether detection of the pair-annihilation gamma rays and detection of the unique gamma ray occurred within a predetermined time or not.

11. The PET device according to claim 10, wherein the imaging processor executes reconstruction of images for the pair-annihilation detection signal differently further according to energy values of gamma rays in the received pair-annihilation detection signal and in the received signal from the energy-resolving gamma ray detector.

12. The PET device according to claim 11,
wherein the imaging processor
executes reconstruction of a distribution image indicating one of the first probe and the PET probe based on events that are not accompanied by detection of the unique gamma ray within the predetermined time in the pair-annihilation detection signal from the energy-resolving gamma ray detector and
executes reconstruction of another distribution image indicates the first probe based on events that are accompanied by detection of the unique gamma ray within the predetermined time in the pair-annihilation detection signal from the energy-resolving gamma ray detector.

13. The PET device according to claim 10,
wherein the imaging processor
executes reconstruction of a distribution image indicating one of the first probe and the PET probe based on events that are not accompanied by detection of the unique gamma ray within the predetermined time in the pair-annihilation detection signal from the energy-resolving gamma ray detector and
executes reconstruction of another distribution image indicates the first probe based on events that are accompanied by detection of the unique gamma ray within the predetermined time in the pair-annihilation detection signal from the energy-resolving gamma ray detector.

14. The PET device according to claim 10,
wherein a gamma ray detector that works as the energy-resolving gamma ray detector is a gamma ray detector provided separately from the group of the PET gamma ray detectors.

15. The PET device according to claim 10,
wherein a gamma ray detector that works as the energy-resolving gamma ray detector is at least one gamma ray detector in the group of the PET gamma ray detectors.

16. The PET device according to claim 10,
wherein the group of PET gamma ray detectors is a group of scintillation detectors.

17. The PET device according to claim 10,
wherein the group of PET gamma ray detectors is a group of semiconductor gamma ray detectors.

18. The PET device according to claim 10,
wherein the energy-resolving gamma ray detector is a scintillation detector.

19. The PET device according to claim 10,
wherein the energy-resolving gamma ray detector is a semiconductor gamma ray detector.

20. The PET device according to claim 10,
wherein the energy-resolving gamma ray detector is provided with a shield for shielding gamma rays coming from outside of filed-of-view for the group of PET detectors.

21. The PET device according to claim 10,
wherein the energy-resolving gamma ray detector is arranged in such a way that any straight line connecting each energy-resolving gamma ray detector and each PET detector does not pass through field-of-view for the group of PET detectors.

22. A method for imaging a plurality of probes in a positron emission tomography (PET) device comprising steps of:
coincidence measurement using a group of PET gamma ray detectors for a pair of pair-annihilation gamma rays from a subject to be imaged, wherein the pair of pair-annihilation gamma rays have been generated by a positron-electron pair annihilation, and wherein to the subject to be imaged both of a first probe and a second probe were administered, the first probe having a nuclide that becomes an excited state of a daughter nuclide through beta decay and, following a positron emission by the beta decay, emits a unique gamma ray of a first energy during transition into a ground state of the daughter nuclide, and the second probe having a nuclide that becomes an excited state of a daughter nuclide through beta decay and, following a positron emission by the beta decay, emits a unique gamma ray of a second energy during transition into a ground state of the daughter nuclide,
performing measurement using an energy-resolving gamma ray detector that is adapted to detect one of the unique gamma rays for resolving the first energy and the second energy, and
imaging processing for receiving both of a pair-annihilation detection signal supplied according to the coincidence measurement with a pair of PET gamma ray detectors in the group of PET gamma ray detectors and a signal supplied by the energy-resolving gamma ray detector, and for executing reconstruction of images for the pair-annihilation detection signal differently according to whether an energy value of a unique gamma ray detected within a predetermined time of the detection of the pair-annihilation gamma rays corresponds to the first energy or the second energy.

23. The method for imaging according to claim 22,
wherein the nuclide in the first probe is any nuclide selected from the nuclide group consisting of $^{14}$O, $^{38}$K, $^{44}$Sc, $^{48}$V, $^{52m}$Mn, $^{60}$Cu, $^{76}$Br, $^{82}$Rb, $^{94m}$Tc, $^{124}$I, and $^{22}$Na, and
wherein the nuclide in the second probe is another nuclide.

24. A method for imaging a plurality of probes in a positron emission tomography (PET) device comprising steps of:
coincidence measurement using a group of PET gamma ray detectors for a pair of pair-annihilation gamma rays from a subject to be imaged, wherein the pair of pair-annihilation gamma rays have been generated by a positron-electron pair annihilation, and wherein to the subject to be imaged both of a first probe and a PET probe were administered, the first probe having a nuclide that becomes an excited state of a daughter nuclide through beta decay and, following a positron emission by the beta decay, emits a unique gamma ray during transition into a ground state of the daughter nuclide, and the PET probe having a positron emitting nuclide that mainly becomes a ground state of a daughter nuclide through the beta decay;
performing measurement using an energy-resolving gamma ray detector for the unique gamma ray emitted by the first probe; and
imaging processing for receiving both of a pair-annihilation detection signal supplied according to the coincidence measurement with a pair of PET gamma ray detectors in the group of PET gamma ray detectors and a signal supplied by the energy-resolving gamma ray detector, and for executing reconstruction of images for the pair-annihilation detection signal differently according to whether detection of the pair-annihilation gamma rays and detection of the unique gamma ray occurred within a predetermined time or not.

25. The method for imaging a plurality of probes according to claim 24,
wherein the step of imaging processing is to execute reconstruction of images for the pair-annihilation detection signal differently further according to energy values of gamma rays in the received pair-annihilation detection signal and in the received signal from the energy-resolving gamma ray detector.

26. The method for imaging according to claim 25, wherein the step of imaging processing includes
- a step of executing reconstruction of a distribution image indicating at least one of the first probe and the PET probe based on events that are not accompanied by detection of the unique gamma ray within the predetermined time in the pair-annihilation detection signal supplied by the energy-resolving gamma ray detector and
- a step of executing reconstruction of a distribution image indicating the first probe based on events that are accompanied by detection of the unique gamma ray within the predetermined time in the pair-annihilation detection signal from the energy-resolving gamma ray detector.

27. The method for imaging according to claim 24, wherein the step of imaging processing includes
- a step of executing reconstruction of a distribution image indicating at least one of the first probe and the PET probe based on events that are not accompanied by detection of the unique gamma ray within the predetermined time in the pair-annihilation detection signal supplied by the energy-resolving gamma ray detector and
- a step of executing reconstruction of a distribution image indicating the first probe based on events that are accompanied by detection of the unique gamma ray within the predetermined time in the pair-annihilation detection signal from the energy-resolving gamma ray detector.

28. The method for imaging according to claim 24, wherein the nuclide in the first probe is any nuclide selected from the nuclide group consisting of $^{14}$O, $^{38}$K, $^{44}$Sc, $^{48}$V, $^{52m}$Mn, $^{60}$Cu, $^{76}$Br, $^{82}$Rb, $^{94m}$Tc, $^{124}$I, and $^{22}$Na.

\* \* \* \* \*